United States Patent
Verkman et al.

(10) Patent No.: US 11,591,304 B2
(45) Date of Patent: Feb. 28, 2023

(54) SLC26A3 INHIBITORS AND USE THEREOF

(71) Applicant: THE REGENTS OF THE UNIVERSITY OF CALIFORNIA, Oakland, CA (US)

(72) Inventors: Alan S. Verkman, Oakland, CA (US); Onur Cil, Oakland, CA (US); Peter M. Haggie, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/050,393

(22) PCT Filed: Apr. 25, 2019

(86) PCT No.: PCT/US2019/029219
§ 371 (c)(1),
(2) Date: Oct. 23, 2020

(87) PCT Pub. No.: WO2019/210103
PCT Pub. Date: Oct. 31, 2019

(65) Prior Publication Data
US 2021/0363123 A1  Nov. 25, 2021

Related U.S. Application Data

(60) Provisional application No. 62/662,574, filed on Apr. 25, 2018.

(51) Int. Cl.
C07D 311/18 (2006.01)
A61P 13/02 (2006.01)
A61P 13/12 (2006.01)

(52) U.S. Cl.
CPC ............ *C07D 311/18* (2013.01); *A61P 13/02* (2018.01); *A61P 13/12* (2018.01)

(58) Field of Classification Search
CPC ......... C07D 311/18; A61P 13/02; A61P 13/12
See application file for complete search history.

(56) References Cited

FOREIGN PATENT DOCUMENTS

WO     2010/056914 A1      5/2010
WO     WO 2010/056914 A1 * 5/2010

OTHER PUBLICATIONS

Nagorichna 43(1) Chem. Nat. Compounds, 10-14 (2007) (CAS Abstract) (Year: 2007).*
Medina-Franco et al., 15(2) Molecular Diversity 293-304 (2011) (CAS Abstract) (Year: 2011).*
Li et al., 55(24) J. Med. Chem. 10896-10908 (2012) (CAS Abstract) (Year: 2012).*
By Lindh et al., 55(2) J. Chem. Info. & Modeling, 343-353 (2015) (CAS Abstract) (Year: 2015).*
Marzaro et al., 19(3) Molecular Diversity, 551-561 (2015) (CAS Abstract) (Year: 2015).*
Kahremany 83(5) CHEMPLUSCHEM 320-333 (2018) (Year: 2018).*
Chernova et al., "Acute regulation of the SLC26A3 congenital chloride diarrhoea anion exchanger (DRA) expressed in *Xenopus* oocytes," *J. Physiol.* 549.1:3-19, 2003, (17 pages).
Haggie et al., "SLC26A3 inhibitor identified in small molecule screen blocks colonic fluid absorption and reduces constipation," *JCI Insight* 3(14):e121370, 2018, (13 pages).
International Search Report and Written Opinion for International Application No. PCT/US2019/029219, dated Dec. 13, 2019, (24 pages).
Lee et al., "4,8-Dimethylcoumarin Inhibitors of Intestinal Anion Exchanger slc26a3 (Downregulated in Adenoma) for Anti-Absorptive Therapy of Constipation," *J. Med. Chem.* 62:8330-8337, 2019, (8 pages).
Li et al., "Coumarin-Based Inhibitors of *Bacillus anthracis* and *Staphylococcus aureus* Replicative DNA Helicase: Chemical Optimization, Biological Evaluation, and Antibacterial Activities," *J. Med. Chem.* 55:10896-10908, 2012, (13 pages).
Lindh et al., "Toward a Benchmarking Data Set Able to Evaluate Ligand- and Structure-based Virtual Screening Using Public HTS Data," *J. Chem. Inf. Model.* 55:343-353, 2015, (11 pages).
Pubchem, "AntiMycobacterium tuberculosis activity 1-week GAST/Fe MIC (uM)," AID: 1314376, Sep. 6, 2018, (5 pages).
Pubchem, "Dose Response confirmation of uHTS hits for Scp-1 phosphatase using a colorimetric assay," AID: 540297, Jul. 23, 2011, (9 pages).
PubChem, "High Throughput Screen of 100,000 compound library to Identify Inhibitors of Mycobacterium tuberculosis H37Rv," AID: 1949, Sep. 18, 2009, (7 pages).
Pubchem, "qHTS for Inhibitors of Glutaminase (GLS)," AID: 624170, May 22, 2012, (7 pages).

* cited by examiner

*Primary Examiner* — Timothy R Rozof
(74) *Attorney, Agent, or Firm* — Seed IP Law Group LLP

(57) ABSTRACT

Provided herein are inhibitors of SLC26A3, which is an anion (CV, HCO$_3$, oxalate) exchanger expressed in intestinal epithelial cells. SLC26A3 inhibitors have potential utility for treatment of constipation including chronic idiopathic constipation (CIC), opioid-induced constipation (OIC), constipation-predominant irritable bowel syndrome (IBS-C), cystic fibrosis-associated constipation, meconium ileus, distal intestinal obstruction syndrome, calcium oxalate kidney stone disease, enteric hyperoxaluria and primary hyperoxalurias.

13 Claims, 18 Drawing Sheets

SLC26A3 INHIBITORS AND USE THEREOF

STATEMENT OF GOVERNMENT INTEREST

This invention was made with government support under Grant Nos. DK099803 and DK072517 awarded by the National Institutes of Health. The government has certain rights in the invention.

BACKGROUND

Technical Field

This disclosure is related to selective inhibitors of an anion exchanger in the colon and use thereof.

Description of the Related Art

Constipation is a common problem with an estimated prevalence of ~15% in the US population. Most common types of chronic constipation include chronic idiopathic constipation (CIC), opioid-induced constipation (OIC), and constipation-predominant irritable bowel syndrome (IBS-C). Current treatment approaches for chronic constipation include lifestyle and dietary changes, over-the-counter laxatives (e.g., stimulants of intestinal contraction, osmotic agents), and recently approved prescription drugs that promote intestinal fluid secretion. Three pro-secretory drugs that activate Cl⁻ channels have been approved: lubiprostone, a prostaglandin derivative that indirectly activates cystic fibrosis transmembrane regulator (CFTR) and chloride channel 2 (ClC-2); linaclotide, a peptide agonist of the guanylate cyclase C receptor that indirectly activates CFTR; and plecanatide, a uroguanylin analog that also acts as an agonist of the guanylate cyclase C receptor. CFTR activators have been shown to have marked pro-secretory action and improved efficacy over lubiprostone and linaclotide in experimental animal models of constipation. See Cil O, Phuan P-W, Lee S, et al. CFTR activator increases intestinal fluid secretion and normalizes stool output in a mouse model of constipation. *Cell Mol Gastroentrol* 2016; 2:317-27. Cil O, Phuan P-W, Son J H, et al. Phenylquinoxalinone CFTR activator as potential prosecretory therapy for constipation. TranslRes 2016; 182:14-26.e4. Son J H, Zhu J S, Phuan P-W, et al. High-potency phenylquinoxalinone cystic fibrosis transmembrane conductance regulator (CFTR) activators. *J Med Chem* 2017; 60:2401-210.

Inhibition of intestinal fluid absorption represents an alternative approach to the pro-secretory mechanism of increasing stool hydration to treat constipation. Recent evaluation of the NHE3 inhibitor tenapanor in a Phase 3 clinical trial for IBS-C showed limited efficacy, with 27% combined pain and stool pattern response rate for the treated group versus 18.7% for placebo. NHE3 is expressed in the small intestine and proximal colon, but not in distal colon. The clinical efficacy of NHE3 inhibition for constipation is thus limited, likely due to unimpaired downstream fluid absorption in distal colon. Bharucha A E, Wouters M M, Tack J. Existing and emerging therapies for managing constipation and diarrhea. *Curr Opin Pharmacol* 2017; 37:158-66.

Kidney stone disease is a common problem with life-time prevalence greater than 12% in men and greater than 6% in women in the US. The recurrence rate of kidney stone disease is very high with 30-40% of patients forming at least another stone in 5 years. Increased urinary oxalate (hyperoxaluria) is a major risk factor for calcium oxalate kidney stones, the most common type of kidney stones affecting approximately 65% of kidney stone patients. It has been recognized that occurrence of calcium oxalate stones could be reduced by lowering urinary oxalate excretion (e.g., decreasing dietary intake of oxalate or vitamin C consumption). Holmes R P, Knight J, Assimos D G. Lowering urinary oxalate excretion to decrease calcium oxalate stone disease. *Urolithiasis* 2016; 44:27-32. However, there is currently no effective therapy for treating calcium oxalate kidney stone diseases due to an apparent lack of biological control of oxalate absorption and excretion, with the end result of nearly all of the oxalate absorbed being excreted in urine.

Heightened oxalate level in urine is the main pathology for enteric hyperoxaluria and primary hyperoxalurias, both of which could ultimately lead to kidney diseases. Currently there are no approved drugs for primary hyperoxalurias and patients are managed with hemodialysis, liver and kidney transplantation.

Accordingly, there remains a need in the art for improved therapy for treating constipation, hyperoxaluria and kidney stones.

BRIEF SUMMARY

Provided herein are inhibitors of SLC26A3, a major anion (Cl⁻, HCO₃⁻, oxalate) exchanger in colon. By selectively targeting SLC26A3, compounds and compositions disclosed herein are shown to be effective in inhibiting intestinal fluid absorption and oxalate absorption. Compounds and compositions according to embodiments disclosed herein provide inhibition potency and metabolic stability.

In particular, inhibition of intestinal fluid absorption was demonstrated in closed intestinal loops in mice, and efficacy was demonstrated in an experimental model of constipation. Moreover, SLC26A3 inhibition and NHE3 inhibition appear to provide an additive or synergistic effect, which can be highly effective in treating refractory constipation.

Furthermore, SLC26A3 inhibition is demonstrated herein as an effective therapy for preventing or treating hyperoxaluria and renal failure by decreasing the amount of oxalate excreted in urine, which is achieved by inhibiting the intestinal absorption of oxalate and removing the unabsorbed oxalate through stool, instead of urine.

Accordingly, one embodiment provides a pharmaceutical composition comprising a pharmaceutically acceptable excipient and a compound of Formula (I):

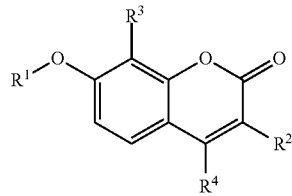

Formula (I)

or a pharmaceutically acceptable salt, isotopic form, stereoisomer or prodrug thereof, wherein:

$R^1$ is optionally substituted $C_1$-$C_6$ alkyl, optionally substituted $C_1$-$C_6$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)₂aryl (wherein aryl is optionally substituted), or optionally substituted arylalkyl;

$R^2$ is carboxy$C_1$-$C_3$alkyl;

$R^3$ is $C_1$-$C_4$ alkyl; and $R^4$ is $C_1$-$C_4$ alkyl, provided that when $R^2$ is carboxyethyl, $R^1$ is substituted benzyl, or when $R^2$ is carboxymethyl, $R^3$ and $R^4$ are each methyl, $R^1$ is not benzyl.

Another embodiment provides a pharmaceutical composition comprising a physiologically acceptable excipient and a compound of Formula (II):

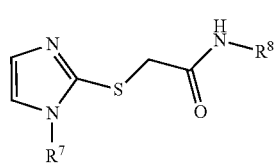

Formula (II)

or a pharmaceutically acceptable salt, isotopic form, stereoisomer or prodrug thereof, wherein:

$R^7$ is optionally substituted aryl; and $R^8$ is optionally substituted aryl.

Other embodiments provide methods for treating or preventing a condition, disease, or disorder associated with SLC26A3-mediated anion (Cl$^-$, HCO$_3^-$, oxalate) exchange, for example chronic idiopathic constipation (CIC), opioid-induced constipation (OIC), and constipation-predominant irritable bowel syndrome (IBS-C), CF-associated constipation, meconium ileus, distal intestinal obstruction syndrome, calcium oxalate kidney stone disease, enteric hyperoxaluria and primary hyperoxaluria. The method comprises administering to a subject in need of the treatment or prevention a therapeutically effective amount of a compound of Formula (I):

Formula (I)

[Chemical structure of Formula (I)]

or a pharmaceutically acceptable salt, isotopic form, stereoisomer or prodrug thereof, wherein:

$R^1$ is optionally substituted $C_1$-$C_6$ alkyl, optionally substituted $C_1$-$C_6$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)$_2$aryl (wherein aryl is optionally substituted), or optionally substituted arylalkyl;

$R^2$ is carboxy$C_1$-$C_3$alkyl;

$R^3$ is $C_1$-$C_4$ alkyl; and $R^4$ is $C_1$-$C_4$ alkyl.

In particularly preferred embodiments, the compounds of Formula (I) are:

Compound A1 (DRA$_{inh}$-A250)

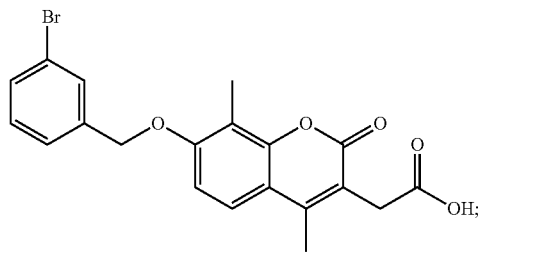

DRA$_{inh}$-A260

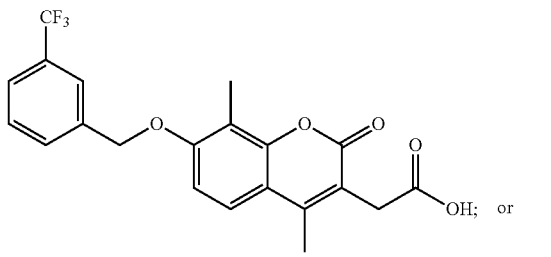

DRA$_{inh}$-A270

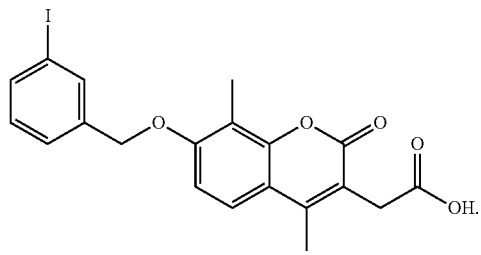

In another embodiment, the method comprises administering to a subject in need of the treatment a therapeutically effective amount of a compound of Formula (II):

Formula (II)

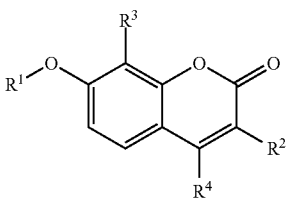

or a pharmaceutically acceptable salt, isotopic form, stereoisomer or prodrug thereof, wherein:

$R^7$ is optionally substituted aryl; and $R^8$ is optionally substituted aryl.

These and other aspects of the invention will be apparent upon reference to the detailed description below.

DETAILED DESCRIPTION

Figure 1:
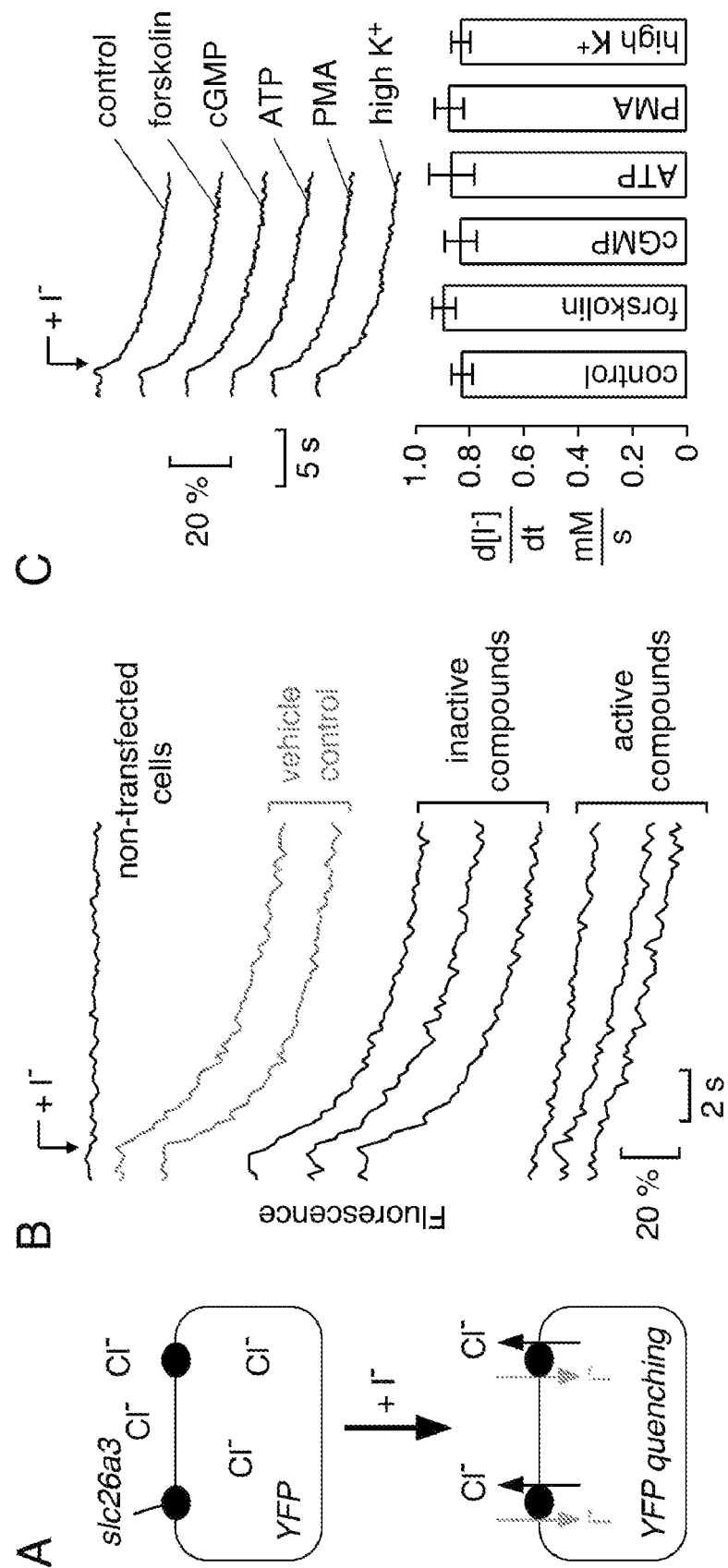
FIG. 1. Assay for high-throughput identification of SLC26A3 inhibitors. A. Assay schematic. Extracellular addition of an I$^-$-containing solution drives slc26a3-mediated Cl$^-$/I$^-$ exchange, resulting in YFP fluorescence quenching. B. Representative fluorescence time course data for non-transfected cells, and slc26a3-transfected cells for vehicle control and inactive and active compounds. C. Absence of slc26a3 regulation by common second messengers, and membrane depolarization. Fluorescence time course data (top) and summary (bottom) for slc26a-mediated $Cl^-/I^-$-exchange under control conditions and after cell treatments to activate cAMP, cGMP, $Ca^{2+}$, or phorbol ester signaling, or depolarization (mean±S.E.M., n=4, differences not significant).

SLC26A3, originally named DRA (down-regulated in adenoma) is an anion ($Cl^-$, $HCO_3^-$, oxalate) exchanger that is expressed in the luminal membrane of intestinal epithelial cells where it facilitates electroneutral NaCl absorption and oxalate absorption. DRA loss of function in humans or mice causes chloride-losing diarrhea. SLC26A3 is also the main transporter in the gut for facilitating the absorption of oxalate. DRA knock-out mice have 60% lower serum oxalate levels and 70% lower urine oxalate levels. Thus, embodiments of this disclosure are direct to identifying and optimizing selective SLC26A3 inhibitors effective as anti-absorptive therapy for treating or preventing constipation, hyperoxaluria and kidney stones diseases.

SLC26A3

SLC26A3 is a member of the SLC26 gene family of anion channels and transporters. The closest SLC26A3 homolog, SLC26A4 (pendrin; 45% amino acid identity), is an anion exchanger in the inner ear, thyroid, inflamed airways and kidney. Certain small-molecule pendrin inhibitors are known to increase airway surface liquid depth in airway epithelial cell cultures and produced a diuretic response in mice, suggesting potential therapeutic utility in inflammatory lung disorders, such as CF and asthma, and in volume-overload edema. See e.g., WO2017/147523. The second most closely related SLC26A3 homolog, SLC26A6 (PAT-1, putative anion transporter-1; 34% amino acid identity), is also an anion exchanger expressed at the apical membrane in small intestine that, together with SLC26A3, facilitates electroneutral NaCl absorption.

SLC26A3 is an anion exchanger expressed at the lumen-facing plasma membrane of enterocytes in colon and small intestine. SLC26A3 facilitates exchange of various monovalent anions, including $Cl^-$, $HCO_3^-$ and thiocyanate ($SCN^-$), as well as the divalent anion oxalate. SLC26A3-mediated $Cl^-/HCO_3^-$ exchange is involved in electroneutral NaCl absorption, which drives water absorption in colon and small intestine. Loss-of-function mutations in SLC26A3 cause congenital chloride-losing diarrhea (CLD) in humans, which is characterized by severe diarrhea that starts in utero. In mice, knockout of slc26a3 recapitulates CLD, producing diarrhea and metabolic alkalosis. SLC26A3 inhibition is thus a potential approach to treating constipation by blocking intestinal fluid absorption, which may be effective in the major types of constipation including opioid-induced constipation, and in constipation associated with cystic fibrosis (CF) in which the pro-secretory cystic fibrosis transmembrane regulator (CFTR) $Cl^-$ channel is defective.

There are at least three pathways for absorption of $Na^+$ and $Cl^-$ in the intestine: nutrient-coupled $Na^+$ absorption, electroneutral NaCl absorption, and electrogenic $Na^+$ absorption. Nutrient-coupled $Na^+$ absorption in small intestine involves sodium-glucose transporters (SGLTs) and Na-amino acid cotransporters in which $Cl^-$ is absorbed through a paracellular pathway. Electroneutral NaCl absorption in small intestine and proximal colon involves $Na^+/H^+$ exchangers (NHE2/SLC9A2 and NHE3) and $Cl^-/HCO_3^-$ exchangers (SLC26A3 and SLC26A6), which are thought to function in tandem to absorb NaCl. Electrogenic $Na^+$ absorption in distal colon involves the epithelial sodium channel (ENaC).

SLC9A3 mutations cause congenital $Na^+$ diarrhea with mild metabolic acidosis, and slc9a3$^{-/-}$ mice have mild diarrhea with luminal fluid alkalinization. However, compensatory increased ENaC activity in distal colon of slc9a3$^{-/-}$ mice is thought to limit the severity of diarrhea. SLC26A3 is mainly expressed in distal colon and duodenum, with low expression in jejunum and ileum, whereas SLC26A6 is mainly expressed in small intestine.

In CF subjects, gastrointestinal-related problems are common, including meconium ileus (~15% occurrence in neonates), constipation (up to 47% lifetime prevalence) and distal intestinal obstructive syndrome (~15% lifetime prevalence). Impaired function of the pro-secretory CFTR $Cl^-$ channel is believed to be the cause of these disorders. It is known that an orally administered CFTR activator was effective in experimental mouse models of constipation; but was ineffective in CF mice lacking functional CFTR.

SLC26A3 is also the main transporter in the gut for facilitating absorption of oxalate, which is present in certain foods and also generated as a metabolic end product in the liver. The majority of oxalate is excreted in urine (90%) with 10% being excreted in stool. Increased urinary oxalate is a major risk factor for calcium oxalate kidney stones (~65% of kidney stone patients).

In calcium oxalate kidney stone disease, the main pathology is high oxalate levels in urine which ultimately leads to kidney disease. The heightened oxalate excretion in urine (hyperoxaluria) could be due to enteric hyperoxaluria or primary hyperoxaluria. Enteric hyperoxaluria is characterized by pathologic hyperabsorption of oxalate in colon due to various gastrointestinal diseases, including bariatric surgery, intestinal resection, inflammatory bowel disease and pancreatic insufficiency. Enteric hyperoxaluria dramatically increases the risk of forming calcium oxalate kidney stones. Primary hyperoxaluria is caused by mutations in genes (AGXT, GRHPR, HOGAI) encoding enzymes in oxalate metabolism pathway and characterized by high plasma and urine oxalate levels. Primary hyperoxaluria ultimately leads to renal failure due to recurrent calcium oxalate stones and calcium oxalate deposition in kidney.

Targeting SLC26A3

SLC26A3 is highly expressed in colon and known to mediate anion exchange. Targeting SLC26A3 is demonstrated herein as an effective therapy for treating or preventing constipation by inhibiting fluid absorption. Similarly, targeting SLC26A3 is shown herein to be effective in preventing hyperoxaluria and kidney stone diseases by mediating or inhibiting oxalate absorption.

As described in more detail throughout this disclosure, screening of 50,000 synthetic small molecules was performed in cells co-expressing murine slc26a3 and a genetically encoded halide sensor. Follow-on structure-activity relationship studies identified potent and selective slc26a3 inhibitors that were characterized in cell and mouse models of constipation and mouse model of oxalate nephropathy induced by high oxalate diet.

Thus, in one embodiment, inhibition of SLC26A3 provides a novel anti-absorptive therapy for constipation. Without wishing to be bound by theory, it is believed that inhibition of SLC26A3, alone or together with drugs acting on alternative anti-absorptive or pro-secretory mechanisms, could be highly effective in treating refractory constipation. Inhibition of SLC26A3 reduced manifestations of constipation with comparable efficiency to a blocker of intestinal $Na^+$ absorption, the NHE3 inhibitor tenapanor, and when co-administered SLC26A3 and NHE3 inhibitors fully reversed constipation.

High-throughput screening identified several classes of SLC26A3 inhibitors, which following structure-activity analysis and optimization produced certain 4,8-dimethylcoumarin compounds, in particular, Compounds A1($DRA_{inh}$-A250), $DRA_{inh}$-A260 and $DRA_{inh}$-A270, with $IC_{50}$ of 100-200 nM for inhibition of SLC26A3-mediated anion exchange. Studies in mice demonstrated these compounds' efficacy in a loperamide model of constipation, and provided novel data that clarified the mechanisms of intestinal fluid absorption. Importantly, the compounds of the present disclosure (e.g., Compound A1) exhibited selective for slc26a3 and did not inhibit homologous slc26a-family anion exchangers or relevant intestinal transporters.

Targeting SLC26A3 has thus proved to be an effective anti-absorptive approach to treating constipation. SLC26A3 inhibitors disclosed herein are shown to have comparable efficacy to tenapanor in a murine model of constipation.

Theoretically, SLC26A3 inhibition could be more effective than NHE3 inhibition for constipation therapy as it blocks absorption in the distal colon where stool is dehydrated to its final form. It is surprisingly found that additive or synergistic actions of NHE3 and SLC26A3 inhibitors in preventing loperamide-induced constipation. The results support that SLC26A3 inhibitors could be effectively used alone as a monotherapy for various types of constipation, or they could be used in combination with NHE3 inhibitors (e.g., tenapanor) in patients that do not respond adequately to monotherapy.

The efficacy of a SLC26A3 inhibitor as constipation therapy is also demonstrated herein in CF mice in a loperamide model of constipation, which supports the conclusion that intestinal SLC26A3 function is not impaired in CF. SLC26A3 inhibition therapy may thus be beneficial in promoting stool hydration and treating constipation in human CF subjects, and potentially in preventing or treating meconium ileus in the neonatal period.

In agreement with these findings, it is disclosed herein that in mouse jejunum that slc26a3 inhibition had no effect while NHE3 inhibition blocked fluid absorption; whereas in mouse distal colon slc26a3 inhibition blocked absorption while NHE3 inhibitor had no effect. These results provide pharmacological evidence that slc26a3 plays little or no role in NaCl absorption in mouse small intestine where Slc26a6 is likely the dominant $Cl^-/HCO_3^-$ exchanger, in agreement with earlier studies.

Though much of the current understanding of intestinal NaCl absorption comes from studies using knock-out mice, it is recognized that knock-out can produce confounding secondary phenotypes because of altered gene expression patterns or organ development. For example, with slc26a4 (pendrin), Applicant found remarkable differences in renal physiology with pharmacological inhibition as compared to $slc26a4^{-/-}$ mice. SLC26A3 loss of function in humans or knockout mice produces CLD with marked diarrhea, whereas the inhibitor studied here had only partial efficacy in a mouse model of constipation. This difference could be due to partial efficacy of the inhibitor, or, perhaps more likely, to secondary phenotypes in the knockout mouse. It is found herein that slc26a3 inhibition blocked fluid absorption only in distal colon supports the latter possibility, as does the additive effect seen on co-administration of slc26a3 inhibitor and tenapanor. An additional contributing factor may be regulatory interactions among NHE3, Slc26a3 and CFTR, that may involve the NHE-regulatory factor (NHERF), SLC26 sulfate transporter antisigma (STAS) domain, and the CFTR regulatory domain. As many CLD-associated SLC26A3 mutations occur in the STAS domain, the severe CLD phenotype might be a consequence of both the loss of SLC26A3 absorption and dysregulation of NHE3 and CFTR activities. Prior studies in subjects with CLD and $slc26a3^{-/-}$ mice showed impaired fluid absorption in the jejunum, whereas closed loop studies here suggested that slc26a3 is of minimal importance in fluid absorption.

The results disclosed herein support the therapeutic utility of SLC26A3 inhibition in promoting stool hydration. Nevertheless, it is further observed that a theoretical relationship exists between SLC26A3 inhibition and tumorigenicity based on the original findings of SLC26A3 down-regulation in adenoma, and manifestation of an expanded colonic epithelial proliferative zone and surface mucosal hyperplasia in $slc26a3^{-/-}$ mice. Notably, however, CLD subjects with SLC26A3 mutations do not manifest an increased incidence of gastrointestinal cancers. Reduced SLC26A3 activity is observed in ulcerative colitis, and single-nucleotide polymorphisms in SLC26A3 have may be a risk factor for development of ulcerative colitis; however, loss of SLC26A3 function does not produce intestinal inflammation as only 6% of CLD subjects report symptoms of Crohn's disease or unspecified colitis. Renal insufficiency is observed in ~25% of CLD subjects, although this likely results from delayed diagnosis and consequent chronic volume and salt depletion. SLC26A3 mutations are also associated with male subfertility, although available evidence suggests impaired SLC26A3-CFTR interaction and consequent impaired CFTR activity are responsible. In general, with appropriate salt replacement therapy, the long-term health in CLD is good, suggesting the absence of significant tumor and non-gastrointestinal problems with SLC26A3 mutation.

In another embodiment, inhibiting SLC26A3 decreases oxalate absorption, thereby protecting kidneys from detrimental effects of hyperoxaluria. $Slc26a3^{-/-}$ mice have greatly decreased oxalate in blood (60% lower) and urine (70% lower) due to impaired oxalate absorption in the gut. Freel R W, Whittamore J M, Hatch M. Transcellular oxalate and Cl-absorption in mouse intestine is mediated by the DRA anion exchanger Slc26a3, and DRA deletion decreases urinary oxalate. *Am J Physiol Gastrointest Liver Physiol* 2013; 305:G520-G527.

Thus, SLC26A3 inhibition is a novel and compelling approach to preventing kidney stones, particularly with respect to calcium-oxalate kidney stones (particularly calcium oxalate kidney stones), treating enteric hyperoxaluria and managing primary hyperoxalurias by facilitating removal of majority of oxalate through stool instead of urine. This is supported by in vivo animal data disclosed herein. In a mouse model of oxalate nephropathy induced by high oxalate diet, slc26a3 inhibition was found to have prevented hyperoxaluria induced by oral sodium oxalate load; development of renal failure, and deposition of renal crystals. These results provide pharmacological evidence that SLC26A3 inhibitors can be effective in treating hyperoxaluria seen in calcium oxalate kidney stone disease, enteric hyperoxaluria and primary hyperoxalurias.

Various embodiments are thus directed to potent SLC26A3 inhibitors, including coumarin derivatives. The SLC26A3 inhibitors according to various embodiments are effective therapies for treating or preventing constipation, hyperoxaluria or kidney stones.

Chemistry Definitions

"Alkyl" means a straight chain or branched, noncyclic, unsaturated or partially unsaturated aliphatic hydrocarbon containing from 1 to 12 carbon atoms. A lower alkyl refers to an alkyl that has any number of carbon atoms between 1 and 6 (i.e., $C_1$-$C_6$ alkyl) Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, tert-pentyl, heptyl, n-octyl, isopentyl, 2-ethylhexyl and the like. Alkyl may be optionally substituted by one or more substituents as defined herein.

"Alkenyl" refers to an unsaturated, straight or branched hydrocarbon chain radical consisting solely of carbon and hydrogen atoms, which contains one or more carbon-carbon double bonds), having from two to twelve carbon atoms ($C_2$-$C_{12}$ alkenyl), preferably one to two carbon atoms ($C_2$-$C_8$ alkenyl) or two to six carbon atoms ($C_2$-$C_6$ alkenyl), and which is attached to the rest of the molecule by a single bond, e.g., ethenyl, prop-1-enyl, but-1-enyl, pent-1-enyl, pent-1,4-dienyl, and the like. Unless stated otherwise specifically in the specification, an alkenyl group is optionally substituted.

"Alkoxy" refers to the radical of —O-alkyl. Examples of alkoxy include methoxy, ethoxy, and the like. The alkyl moiety of alkoxy may be optionally substituted by one or more substituents as defined herein.

"Alkoxyalkyl" refers to a radical of the formula —$R_bOR_a$ where $R_a$ is an alkyl radical as defined above and $R_b$ is an alkylene chain.

"Carboxyalkyl" refers to a straight or branched alkyl radical substituted with —$CO_2H$. The length of the alkyl radical may be indicated by the number of the carbon atoms excluding the carbon of the carboxy moiety, for example, carboxy$C_1$-$C_3$alkyl includes —$CH_2CO_2H$, —$CH_2CH_2CO_2H$, —$CH_2CH_2CH_2CO_2H$, and the like.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms, preferably having from three to ten carbon atoms, or preferably having from three to six ($C_3$-$C_6$) carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl.

"Cycloalkylalkyl" refers to a radical of the formula —$R_bR_c$ where $R_b$ is an alkylene chain and $R_c$ is a cycloalkyl radical as defined above.

"Aryl" means an aromatic carbocyclic moiety such as phenyl or naphthyl (i.e., naphthalenyl) (1- or 2-naphthyl) or anthracenyl (e.g., 2-anthracenyl).

"Arylalkyl" (e.g., phenylalkyl) means an alkyl having at least one alkyl hydrogen atom replaced with an aryl moiety, such as —$CH_2$-phenyl (i.e., benzyl), —CH=CH-phenyl, —C($CH_3$)=CH-phenyl, and the like.

"Heteroaryl" refers to a 5- to 14-membered ring system radical comprising hydrogen atoms, one to thirteen ring carbon atoms, one to six ring heteroatoms selected from the group consisting of nitrogen, oxygen and sulfur, and at least one aromatic ring comprising a heteroatom. For purposes of embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl).

"Heteroarylalkyl" refers to a radical of the formula —$R_bR_d$ where $R_b$ is an alkylene chain and $R_d$ is a heteroaryl radical as defined above.

"Halogen" or "halo" means fluoro, chloro, bromo, and iodo.

"Haloalkyl" refers to a halo-substituted alkyl, i.e., alkyl in which at least one hydrogen atom is replaced with halogen. "Perhaloalkyl" refers to haloalkyl in which all of the hydrogens are replaced by halogens. Examples of haloalkyls include trifluomethyl, difluorobromomethyl, difluorochloromethyl, 1,1,2,2,3,3,3-heptafluoropropyl and the like. In certain embodiments, the halo substituents of a haloalkyl or perhaloalkyl may be the same (e.g., all of the halo substituents are fluoro) or different (e.g., the halo substituents may be a mixture of any two or more of fluoro, chloro, bromo or iodo). The alkyl moiety of a haloalkyl may be optionally substituted by one or more substituents as defined herein.

"Haloalkoxy" refers to a substituted alkoxy, means an alkoxy moiety having at least one hydrogen atom replaced with halogen, such as chloromethoxy and the like.

All the above groups may be "optionally substituted," i.e., either substituted or unsubstituted. The term "substituted" as used herein means any of the above groups (i.e., alkyl, alkoxy, alkoxyalkyl, aryl, aralkyl, heterocyclyl, heterocyclylalkyl, heteroaryl, heteroarylalkyl and/or trifluoroalkyl), may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, —CONH$_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, thioalkyl triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —S OR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently, hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents.

Pharmaceutical Composition

One embodiment provides a pharmaceutical composition comprising a physiologically acceptable excipient and a compound of Formula (I):

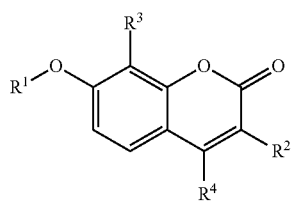

or a pharmaceutically acceptable salt, isotopic form, stereoisomer or prodrug thereof, wherein:

R$^1$ is optionally substituted C$_1$-C$_6$ alkyl, optionally substituted C$_1$-C$_3$ alkenyl, optionally substituted C$_3$-C$_6$ cycloalkyl, optionally substituted C$_3$-C$_6$ cycloalkylalkyl, optionally substituted alkoxyalkyl, carboxyC$_1$-C$_3$alkyl, optionally substituted heteroarylalkyl, —S(O)$_2$aryl (wherein aryl is optionally substituted) or optionally substituted arylalkyl;

R$^2$ is carboxyC$_1$-C$_3$alkyl;

R$^3$ is C$_1$-C$_4$ alkyl; and

R$^4$ is C$_1$-C$_4$ alkyl, provided that when R$^2$ is carboxyethyl, R$^1$ is substituted benzyl, or when R$^2$ is carboxymethyl, R$^3$ and R$^4$ are each methyl, R$^1$ is not benzyl.

In certain embodiments, R$^1$ is optionally substituted benzyl. In some more specific embodiments, R$^1$ has the following structure:

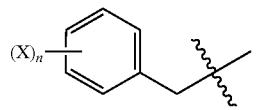

wherein:

X is alkyl, C$_3$-C$_5$ cycloalkyl, halo, haloalkyl, alkoxy, NO$_2$, or haloalkoxy; and n is 1, 2, 3, 4 or 5.

In more specific embodiments, n is 1 or 2, X is bromo, chloro, fluoro, iodo, cyclopropyl, CF$_3$, methyl, NO$_2$ or methoxy.

In more specific embodiments, n is 1, and X is halogen (Br or I) at a meta-location.

In some other embodiments, R$^1$ has one of the following structures:

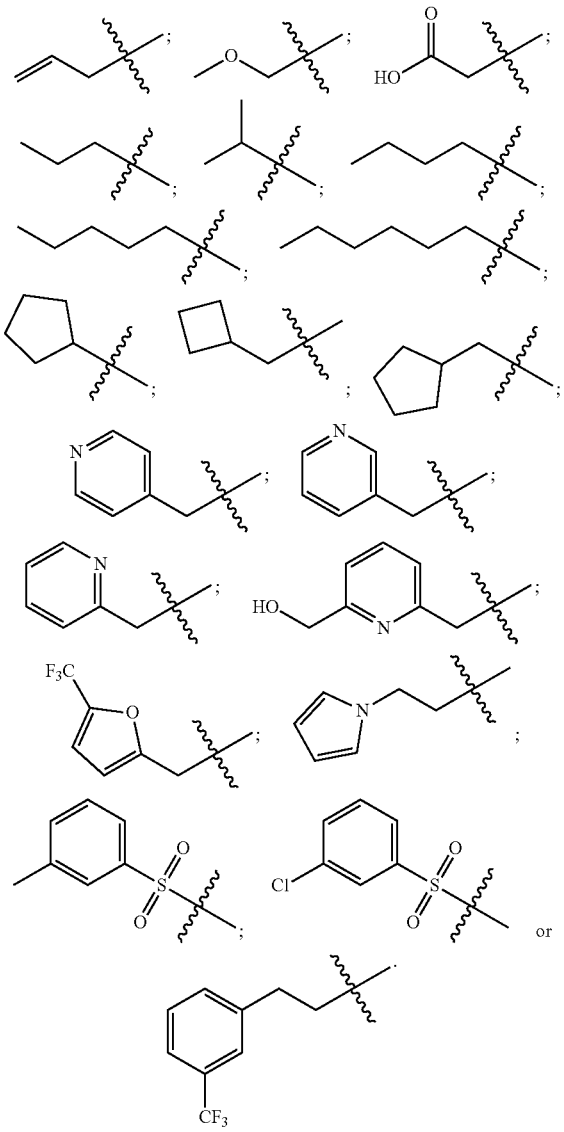

In certain embodiments, $R^2$ is —$CH_2COOH$, or —$CH_2CH_2COOH$:

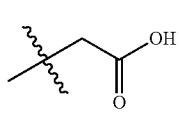 or 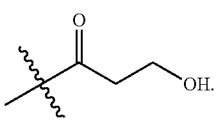

In some embodiments, $R^3$ is methyl. In certain embodiments, $R^4$ is methyl.

In a preferred embodiment, the compounds of Formula (I) is represented by the following Formula (Ia):

Formula (Ia)

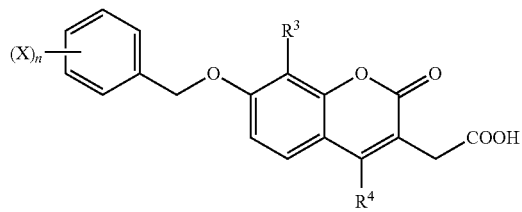

wherein, X is alkyl, $C_3$-$C_5$ cycloalkyl, halo, haloalkyl, alkoxy, $NO_2$, or haloalkoxy; and n is 1, 2, or 3.

More specific embodiments provide compounds of Formula (Ia), wherein n is 1 or 2, X is bromo, chloro, fluoro, iodo, cyclopropyl, $CF_3$, methyl, $NO_2$ or methoxy, and $R^3$ and $R^4$ are each methyl.

In more specific embodiments, the compound of Formula (I) or (Ia) has one of the following structures:

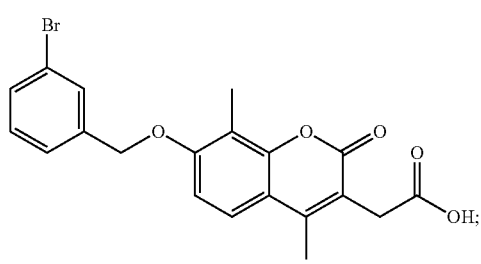

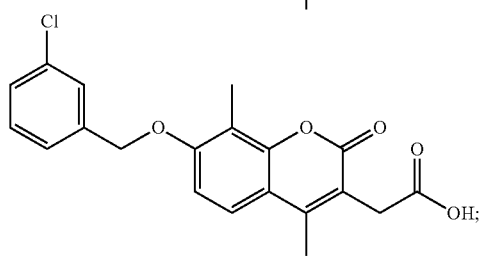

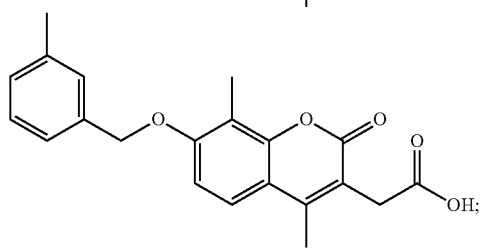

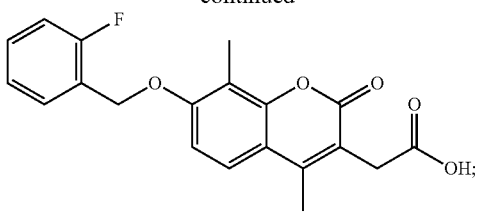

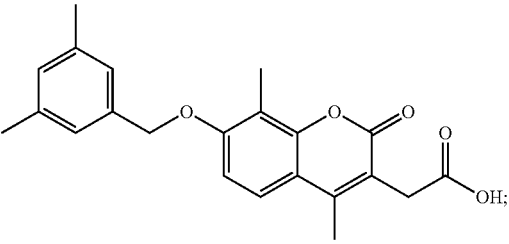

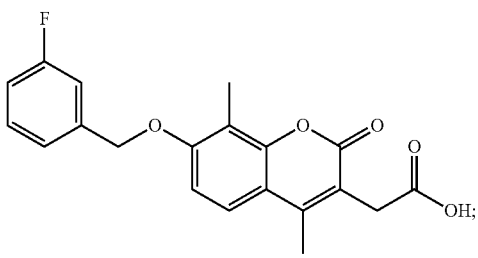

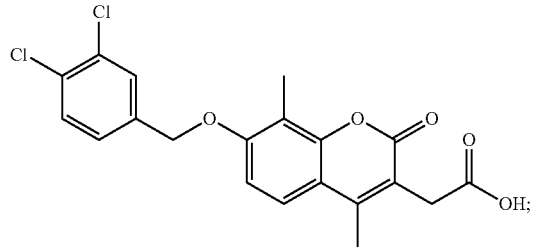

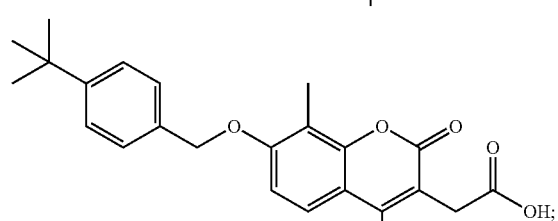

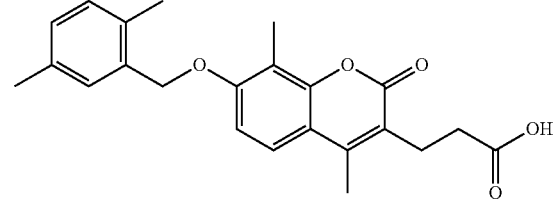

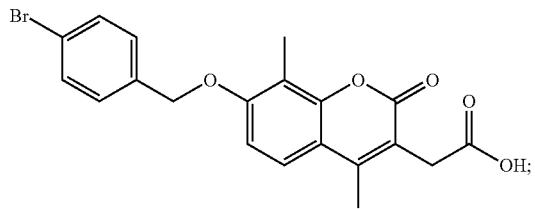

-continued
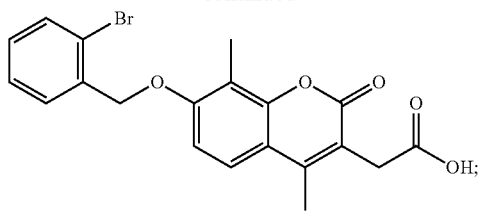
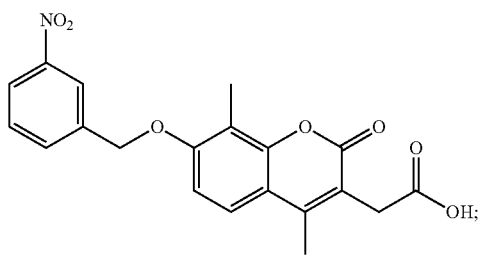
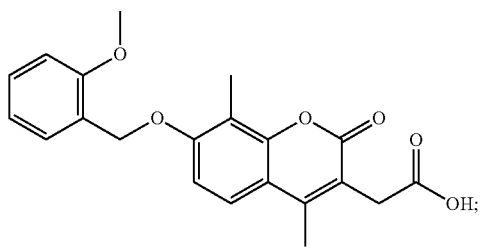
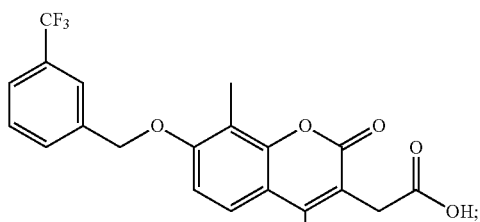
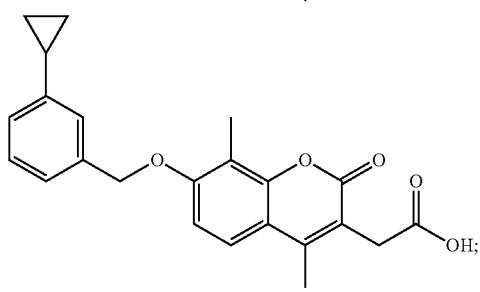
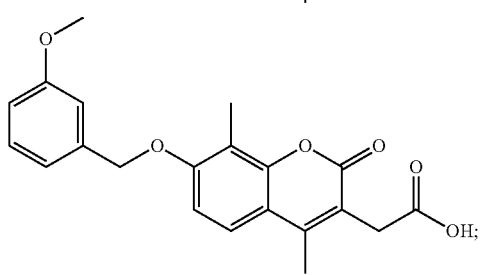
-continued
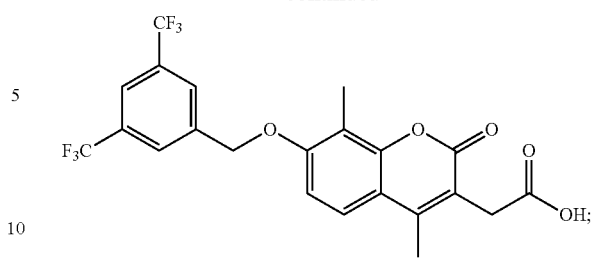
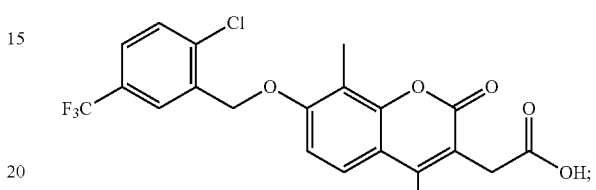
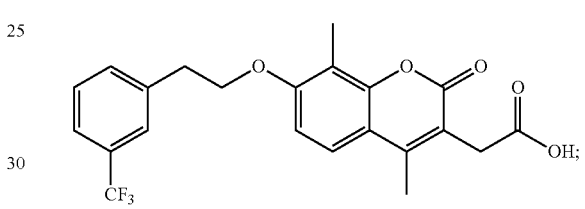
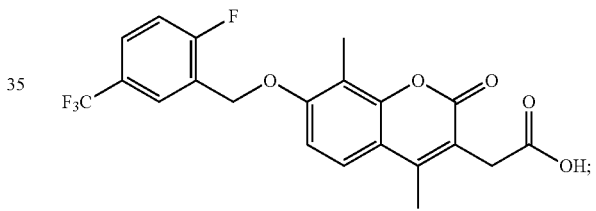
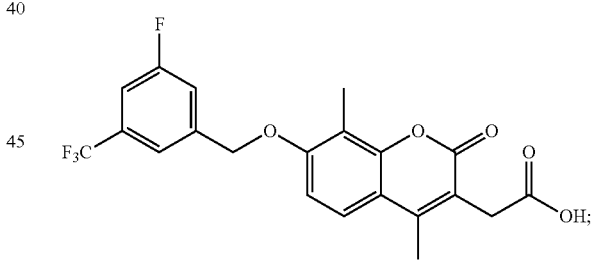
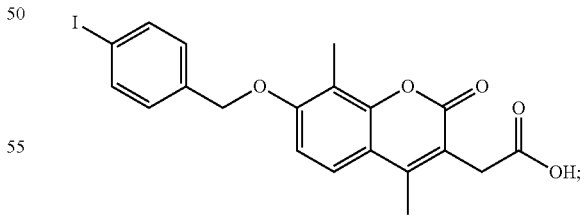
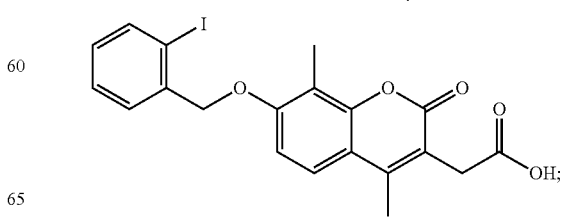

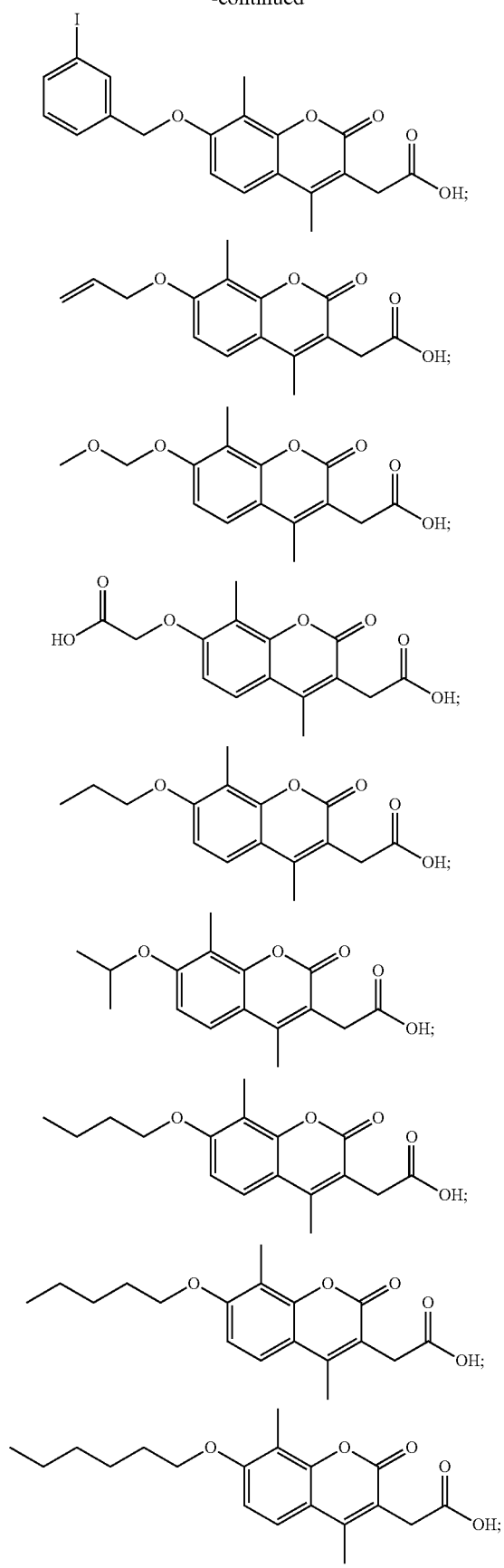
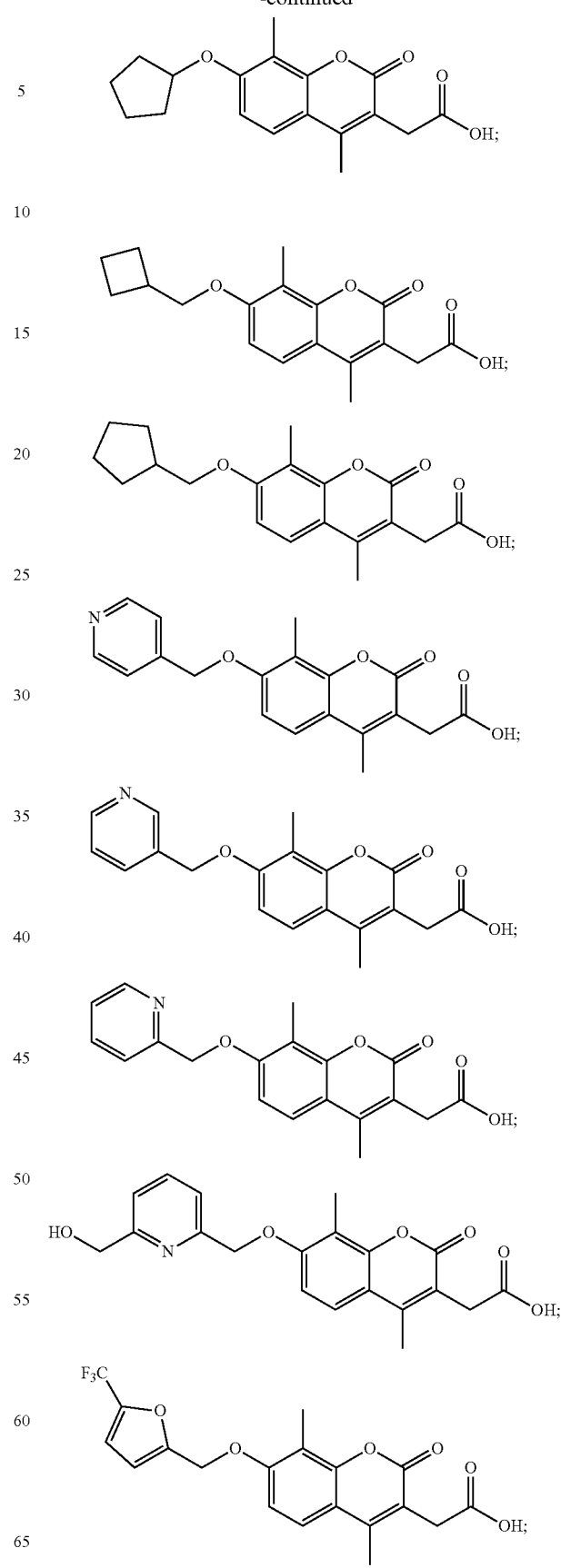

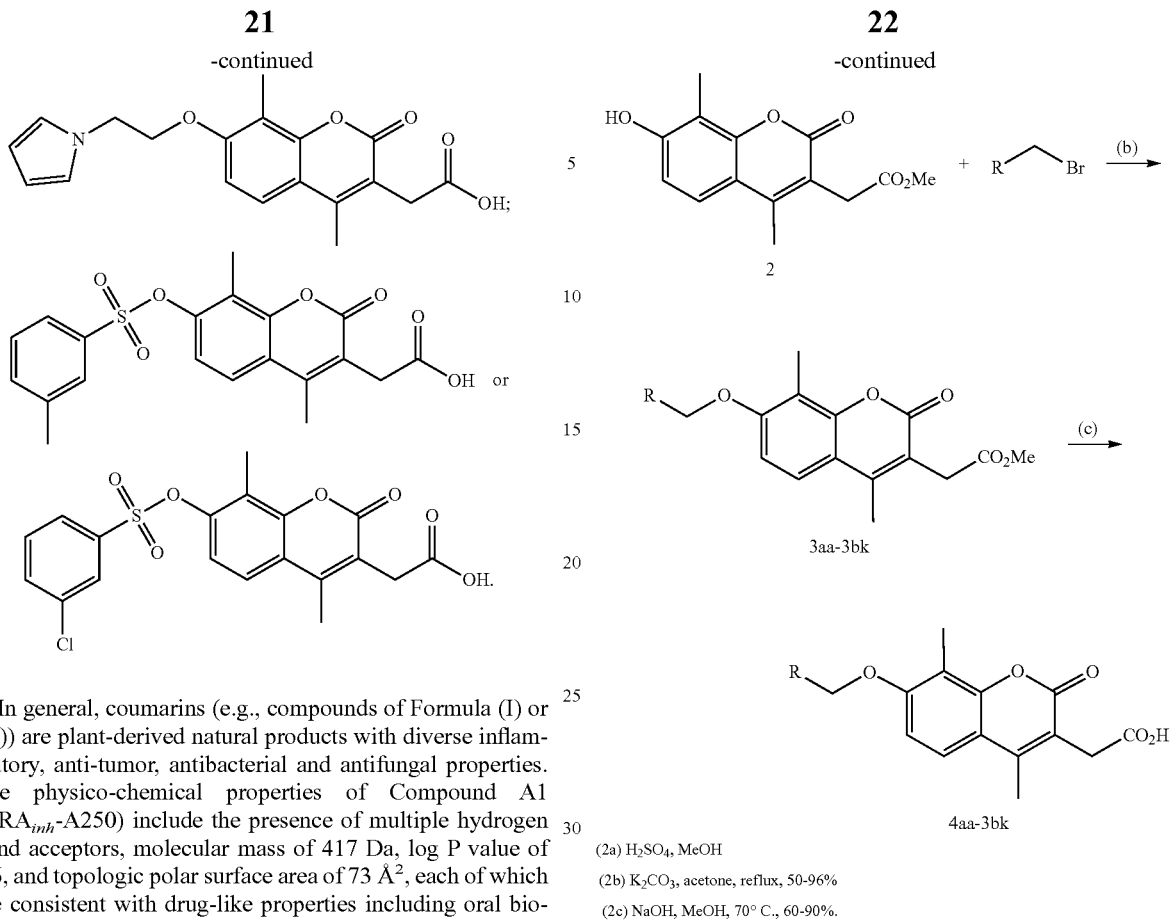

In general, coumarins (e.g., compounds of Formula (I) or (Ia)) are plant-derived natural products with diverse inflammatory, anti-tumor, antibacterial and antifungal properties. The physico-chemical properties of Compound A1 (DRA$_{inh}$-A250) include the presence of multiple hydrogen bond acceptors, molecular mass of 417 Da, log P value of 4.6, and topologic polar surface area of 73 Å$^2$, each of which are consistent with drug-like properties including oral bioavailability. In addition, the 3-acetic-acid-coumarin scaffold does not belong to promiscuous binders known as pan-assay interference compound molecules.

There have been a few prior reports on other biological properties of the 7-benzoxy-4,8-dimethyl-3-acetic acid-coumarin scaffold as found in Compound A1. Similar coumarins were reported as inhibitors of *Bacillus anthracis* and *Staphylococcus aureus* replicative DNA helicase. Li B, Pai R, Di M, et al. Coumarin-based inhibitors of *Bacillus anthracis* and *Staphylococcus aureus* replicative DNA helicase. *J Med Chem* 2012; 55:10896-908. Another 3-acetic acid-coumarin was reported to inhibit the oncogene signal transducer and activator of transcription (Stat3) activation by inhibiting the nuclear translocation of phosphorylated Stat3. Xu X-L, Kasembeli M M, Jiang X, et al. Chemical probes that competitively and selectively inhibit Stat3 activation. *PLoS One* 2009:4(3):e4783.

Synthetically, the 3-acetic-acid-coumarin scaffold can be prepared in 3-5 steps from commercially available starting materials, which allows facile synthesis of targeted analogs. Reaction Scheme 1 represents a synthetic pathway for preparing certain compounds of Formula (I) or (Ia), for instance, the —CH$_2$—R group corresponds to the R$^1$ group of Formula (I).

REACTION SCHEME 1

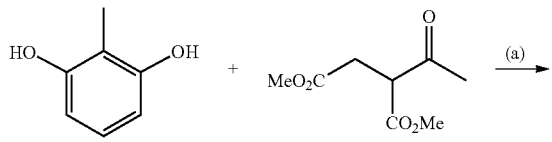

(2a) H$_2$SO$_4$, MeOH (2b) K$_2$CO$_3$, acetone, reflux, 50-96%

(2c) NaOH, MeOH, 70° C., 60-90%.

More specifically, Pechmann reaction of 2-methyl resorcinol with diethyl acetyl succinate under sulfuric acid condition (a) afforded 4,8-dimethyl-7-hydroxycoumarin ester (2, above) quantitatively. Reaction of 2 with alkyl bromide (b) gave 7-alkoxy-4,8-dimethylcoumarin compounds in 80-90% yields. Reaction of 2 with the substituted benzyl bromides gave substituted benzyloxy-4,8-dimethylcoumarin compounds in 50-96% yields. The resultant compounds from steps (b) and (c) were hydrolyzed with 1N sodium hydroxide solution in methanol (2c) furnished representative Class A compounds in 60-90% yields.

Some other embodiments provide a pharmaceutical composition comprising a physiologically acceptable excipient and a compound of Formula (II):

Formula (II)

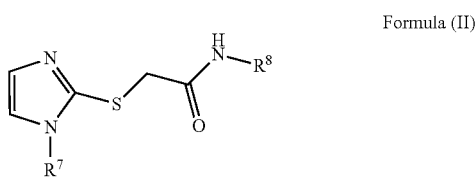

or a pharmaceutically acceptable salt, isotopic form, stereoisomer or prodrug thereof, wherein:

R$^7$ is optionally substituted aryl; and

R$^8$ is optionally substituted aryl.

In some of these embodiments, R$^7$ is optionally substituted phenyl. In more specific embodiments R$^7$ has the following structure:

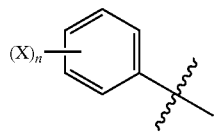

wherein:
X is hydrogen, alkyl, halo, haloalkyl, alkoxy or haloalkoxy; and
n is 0, 1, 2, 3, 4 or 5.

In some embodiments, X is hydrogen, chloro, bromo, methyl, or methoxy and n is 1 or 2.

In some embodiments, $R^7$ is optionally substituted phenyl. In certain specific embodiments, $R^8$ has the following structure:

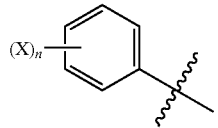

wherein:
X is alkyl, halo, haloalkyl, alkoxy or haloalkoxy; and
n is 1, 2, 3, 4 or 5.

In some embodiments, X is chloro, bromo, methyl, or methoxy and n is 1 or 2.

In some specific embodiments, the compound of Formula (II) has one of the following structures:

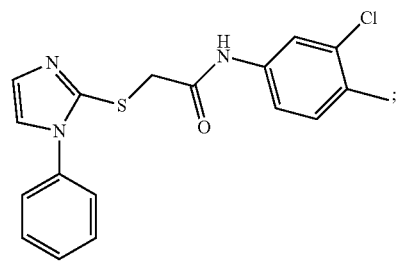

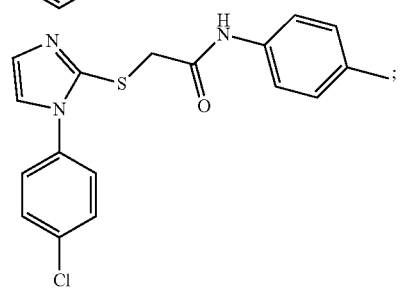

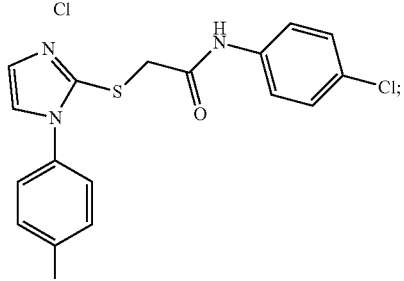

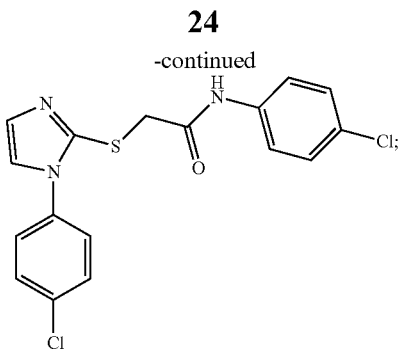

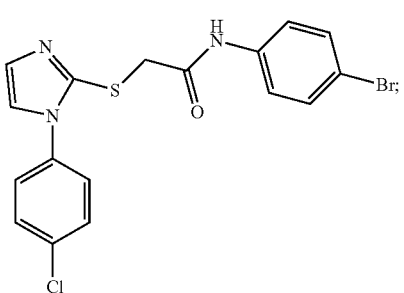

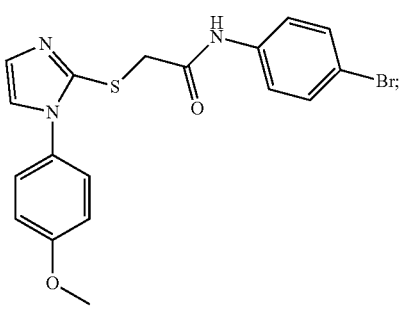

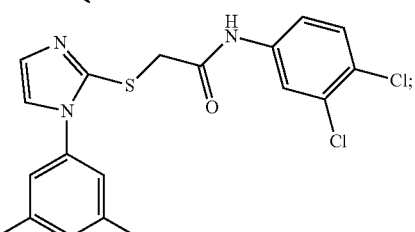

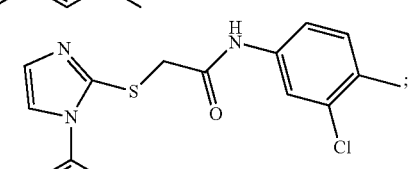

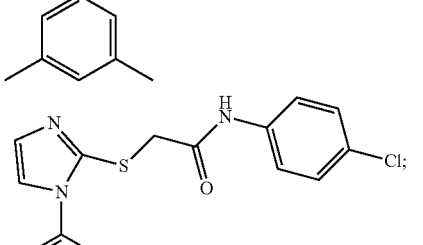

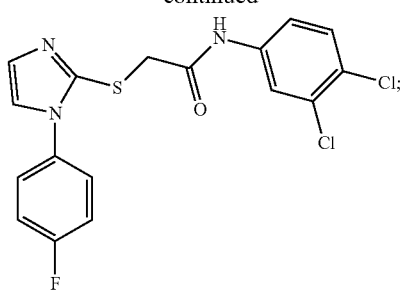
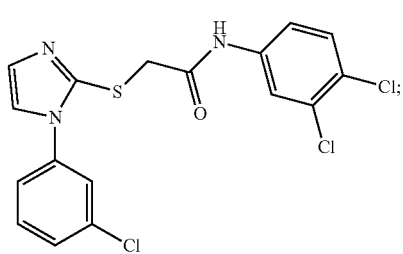
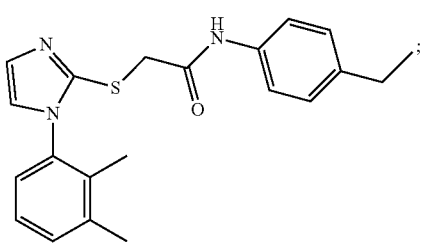
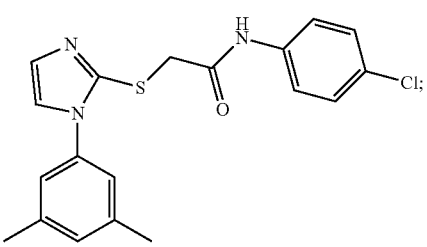
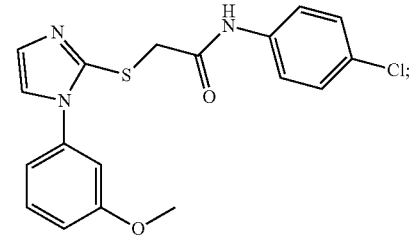
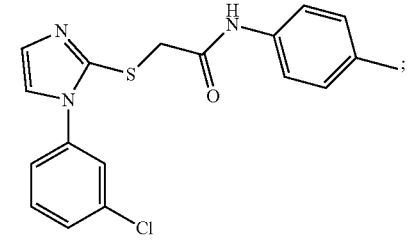
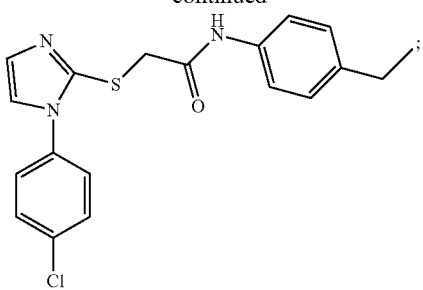
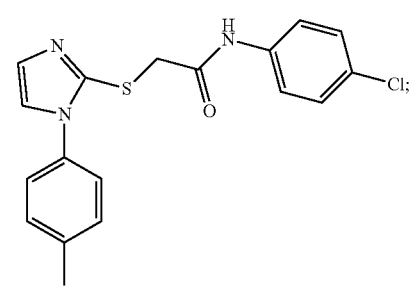
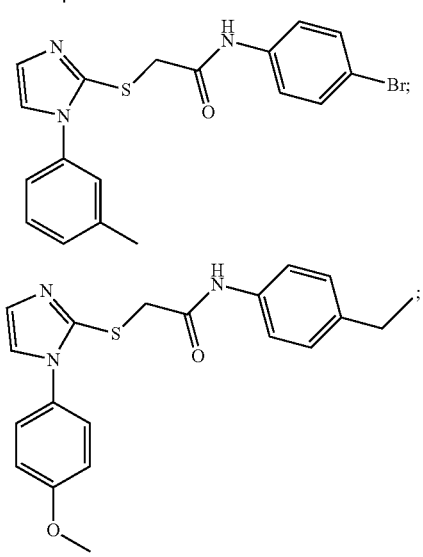
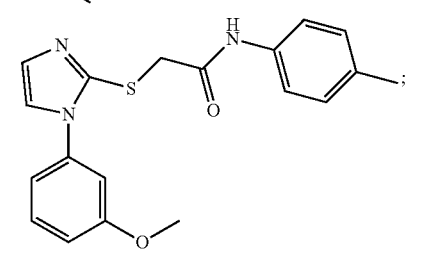
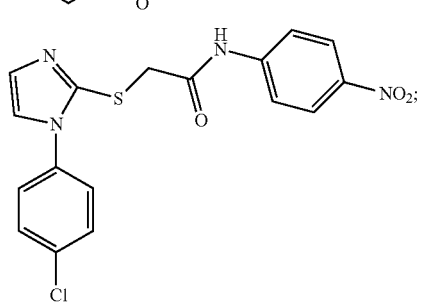

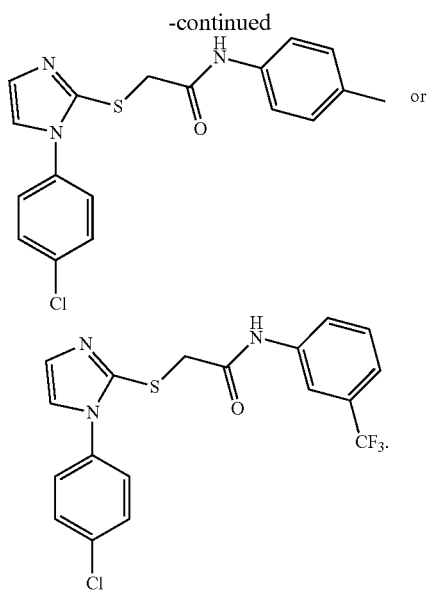

or

A pharmaceutical composition, as used herein, refers to a mixture of a compound described herein with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

A pharmaceutical composition may be a sterile aqueous or non-aqueous solution, suspension or emulsion, which additionally comprises a physiologically acceptable excipient (also called a pharmaceutically acceptable or suitable excipient or carrier) (i.e., a non-toxic material that does not interfere with the activity of the active ingredient). Such compositions may be in the form of a solid, liquid, or gas (aerosol).

In one embodiment, one or more compound is formulated in an aqueous solution. In specific embodiments, the aqueous solution is selected from, by way of example only, a physiologically compatible buffer, such as Hank's solution, Ringer's solution, or physiological saline buffer. In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

Useful pharmaceutical compositions also, optionally, include solubilizing agents to aid in the solubility of a compound described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Use and Method of Treatment

Also provided herein is a method of inhibiting SLC26A3 comprising: contacting (a) a cell that expresses SLC26A3 and (b) a pharmaceutical composition comprising a compound of Formula (I), in an amount effective and under conditions and for a time sufficient to inhibit SLC26A3-mediated anion (Cl⁻, HCO₃⁻, oxalate) exchange, wherein the compound of Formula (I) has the following structure:

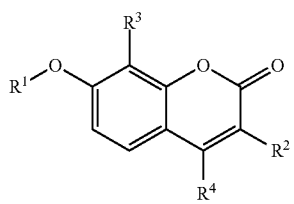

Formula (I)

or a pharmaceutically acceptable salt, isotopic form, stereoisomer or prodrug thereof, wherein:

$R^1$ is optionally substituted $C_1$-$C_6$ alkyl, optionally substituted $C_1$-$C_3$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)₂aryl (wherein aryl is optionally substituted) or optionally substituted arylalkyl;

$R^2$ is carboxy$C_1$-$C_3$alkyl;

$R^3$ is $C_1$-$C_4$ alkyl; and $R^4$ is $C_1$-$C_4$ alkyl.

In a specific embodiment, the cell is an epithelial cell. In a particular embodiment, the epithelial cell is an intestinal epithelial cell or a lung epithelial cell.

In a specific embodiment, the compound has a structure represented by Formula (Ia):

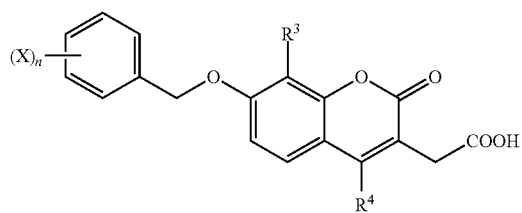

Formula (Ia)

wherein, X is alkyl, $C_3$-$C_5$ cycloalkyl, halo, haloalkyl, alkoxy, NO₂, or haloalkoxy; and n is 1, 2, or 3.

In more specific embodiments, the compound is Compound A1 (DRA$_{inh}$-A250), DRA$_{inh}$-A260 or DRA$_{inh}$-A270, the respective structures of which are shown below:

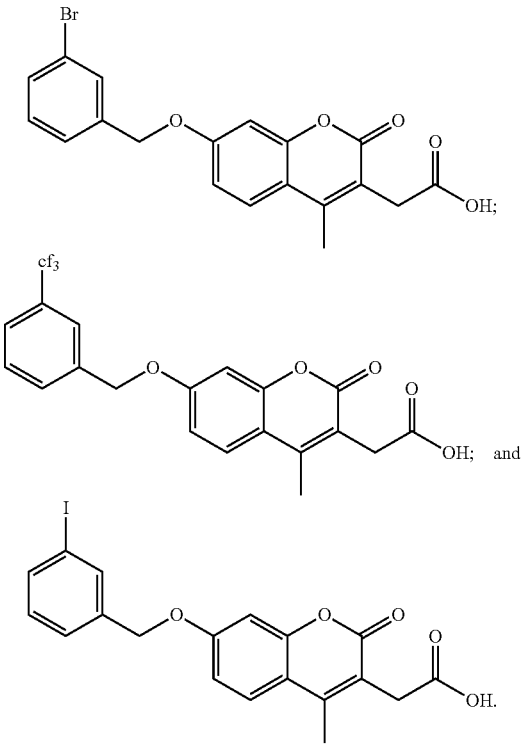

Another embodiment provides a method of preventing or treating a condition, disease, or disorder associated with SLC26A3-mediated anion (Cl⁻, HCO₃⁻, oxalate) exchange, the method comprising administering to a subject in need thereof a compound of Formula (I) in an amount effective to inhibit SLC26A3-mediated anion (Cl⁻, HCO₃⁻, oxalate) exchange, wherein the compound of Formula (I) has the following structure:

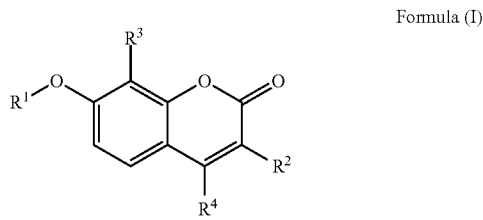

Formula (I)

or a pharmaceutically acceptable salt, isotopic form, stereoisomer or prodrug thereof, wherein:

$R^1$ is optionally substituted $C_1$-$C_6$ alkyl, optionally substituted $C_1$-$C_3$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)₂aryl (wherein aryl is optionally substituted) or optionally substituted arylalkyl;

$R^2$ is carboxy$C_1$-$C_3$alkyl;

$R^3$ is $C_1$-$C_4$ alkyl; and $R^4$ is $C_1$-$C_4$ alkyl.

In one embodiment, the disease or disorder is constipation (e.g., CIC, OIC, and/or IBS-C),CF-associated constipation, meconium ileus, distal intestinal obstruction syndrome, calcium oxalate kidney stone disease, enteric hyperoxaluria or primary hyperoxalurias.

In a specific embodiment, the compound has a structure represented by Formula (Ia):

Formula (Ia)

wherein, X is alkyl, $C_3$-$C_5$ cycloalkyl, halo, haloalkyl, alkoxy, $NO_2$, or haloalkoxy; and n is 1, 2, or 3.

In more specific embodiments, the compound is Compound A1 ($DRA_{inh}$-A250), $DRA_{inh}$-A260 or $DRA_{inh}$-A270.

A further embodiment provides a method of treating constipation, the method comprising administering to a subject in need thereof a therapeutically effective amount of a compound of Formula (I), (Ia) or (II).

In certain embodiments, the constipation is chronic constipation include chronic idiopathic constipation (CIC), opioid-induced constipation (OIC), constipation-predominant irritable bowel syndrome (IBS-C), CF-associated constipation, meconium ileus, distal intestinal obstruction syndrome.

In a specific embodiment, the compound has a structure represented by Formula (Ia):

Formula (Ia)

wherein, X is alkyl, $C_3$-$C_5$ cycloalkyl, halo, haloalkyl, alkoxy, $NO_2$, or haloalkoxy; and n is 1, 2, or 3.

In a more specific embodiment, the compound is Compound A1, $DRA_{inh}$-A260 or $DRA_{inh}$-A270.

In a further embodiment, the method further comprises administering, simultaneously or sequentially with the compound of Formula (I), an NHE3 inhibitor.

In more specific embodiments, NHE3 inhibitor is tenapanor, and the condition or disorder is refractory constipation.

Another embodiment provides a method of decreasing urinary oxalate excretion in a subject in need thereof, the method comprising administering to the subject a therapeutically effective amount of a compound of Formula (I):

Formula (I)

or a pharmaceutically acceptable salt, isotopic form, stereoisomer or prodrug thereof, wherein:

$R^1$ is optionally substituted $C_1$-$C_6$ alkyl, optionally substituted $C_1$-$C_3$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)$_2$aryl (wherein aryl is optionally substituted) or optionally substituted arylalkyl;

$R^2$ is carboxy$C_1$-$C_3$alkyl;
$R^3$ is $C_1$-$C_4$ alkyl; and
$R^4$ is $C_1$-$C_4$ alkyl.

In more specific embodiments, the subject in need of decreasing urinary oxalate excretion suffers from enteric hyperoxaluria or primary hyperoxaluria.

In a specific embodiment, the compound has a structure represented by Formula (Ia):

Formula (Ia)

wherein, X is alkyl, $C_3$-$C_5$ cycloalkyl, halo, haloalkyl, alkoxy, $NO_2$, or haloalkoxy; and n is 1, 2, or 3.

In a more specific embodiment, the compound is Compound A1, $DRA_{inh}$-A260 or $DRA_{inh}$-A270.

Yet another embodiment provides a method of preventing or treating kidney stone, the method comprising administering to a subject in need thereof a therapeutically effective amount of compound of Formula (I) having the following structure:

Formula (I)

or a pharmaceutically acceptable salt, isotopic form, stereoisomer or prodrug thereof, wherein:

$R^1$ is optionally substituted $C_1$-$C_6$ alkyl, optionally substituted $C_1$-$C_3$ alkenyl, optionally substituted $C_3$-$C_6$ cycloalkyl, optionally substituted $C_3$-$C_6$ cycloalkylalkyl, optionally substituted alkoxyalkyl, carboxy$C_1$-$C_3$alkyl, optionally substituted heteroarylalkyl, —S(O)$_2$aryl (wherein aryl is optionally substituted) or optionally substituted arylalkyl;

R$^2$ is carboxyC$_1$-C$_3$alkyl;

R$^3$ is C$_1$-C$_4$ alkyl; and

R$^4$ is C$_1$-C$_4$ alkyl.

In more specific embodiments, the kidney stone is calcium-oxalate kidney stone.

In a specific embodiment, the compound has a structure represented by Formula (Ia).

In more specific embodiments, the compound is Compound A1 (DRA$_{inh}$-A250), DRA$_{inh}$-A260 or DRA$_{inh}$-A270.

In other embodiments, the above methods and uses comprise administering a compound of Formula (II) to a subject in need thereof.

EXAMPLES

Abbreviations

CFTR, cystic fibrosis transmembrane regulator; DCM, dichloromethane; 4-DMAP, N,N-dimethylaminopyridine; DMF, N,N-dimethylformamide; DMSO, dimethyl sulfoxide; EDCI-HCl, 1-(3-dimethylaminopropyl)-3-ethylcarbodiimide hydrochloride; FPR, fluorescent plate reader; FRT, Fischer Rat Thyroid; PBS, phosphate-buffered saline; RT, room temperature; TLC, thin layer chromatography; TMEM16A, transmembrane member 16A; YFP, yellow fluorescent protein.

General Experimental

Unless otherwise indicated, all reaction solvents were anhydrous and obtained as such from commercial sources. Difluoroiodoacetic acid was purchased from Synquest Laboratories (Alachua, Fla.). All other reagents were used as supplied.

All purchased materials and solvents were used without further purification. $^1$H and $^{13}$C NMR spectra were determined on an Avance 300 MHz NMR Spectrometer (Bruker, San Jose, Calif.). Chemical shifts are given in parts per million (ppm). LC-MS analysis was performed using a Micromass ZQ Mass Spectrometer with 2695 HPLC Separations Module (Waters, Milford, Mass.). Compounds tested had >95% purity by LC/MS.

High-throughput screening to identify slc26a3 inhibitors using FRT-YFP-slc26a3 cells was done with a semi-automated Beckman Coulter (Indianapolis, Ind.) platform with FLUOstar OMEGA plate readers (BMG Labtech, Cary, N.C.), essentially as described for discovery of pendrin inhibitors. Initial screening was done of ~50,000 drug-like synthetic small molecules (ChemDiv, San Diego, Calif.) at a concentration of 25 μM using a Cl$^-$/I$^-$ exchange protocol to assay slc26a3 function. Following initial screening, compound analogs were purchased (ChemDiv, San Diego, Calif.) to generate structure-activity data. The lead slc26a3 inhibitor was resynthesized and confirmed by $^1$H and $^{13}$C NMR, and >95% purity was confirmed by LC-MS.

For the screening, FRT-YFP-slc26a3 cells were plated in 96-well black-walled, clear-bottom tissue culture plates (Corning Life Sciences, Tewksbury, Mass.) at a density of 20,000 cells/well and cultured for 48 hours until confluent. For screening, cells were washed twice in PBS and incubated for 10 min in 100 μl PBS containing test compounds prior to assay of slc26a3 function. Assays were done using a FLUOstar OMEGA plate reader (BMG Labtech, Cary, N.C.) over 12 s with initial fluorescence recorded over 1 s prior to addition of 100 μl NaI-substituted PBS (137 mM NaCl replaced by 137 mM NaI) to drive Cl$^-$/I$^-$ exchange. The initial rate of Cl$^-$/I$^-$ exchange was determined from fluorescence intensity by single exponential regression. All plates contained wells with negative (1% DMSO) and positive (350 μM niflumic acid) controls. After initial screening, analogs of active compounds were purchased (ChemDiv) to generate structure-activity relationship data.

Animal experiments were approved by the UCSF Institutional Animal Care and Use Committee (IACUC). Closed-loop models, and the loperamide-induced model of constipation were done in mice using techniques known in the literature. Mice were housed in communal cages with standard rodent chow and water available ad libitum. Wild-type CD1 mice and ΔF508-CFTR homozygous mice were bred in the UCSF Laboratory Animal Resource Center.

Example 1

High-Throughput Screen to Identify Slc26A3 Inhibitors

Screening was done using an FRT cell line stably expressing murine slc26a3 and a halide-sensitive yellow fluorescent protein (FRT-YFP-slc26a3 cells). FRT cells were used because of their low intrinsic permeability to anions that are transported by slc26a3, and because of their good adherence and rapid growth on uncoated plastic. As diagrammed in FIG. 1A, slc26a3-mediated transport was assayed from the kinetics of YFP fluorescence quenching in response to extracellular addition of I$^-$ to drive Cl$^-$/I$^-$ exchange; transport inhibition reduces the rate of fluorescence decrease. FIG. 1B shows representative fluorescence data from inactive and active compounds tested in screening, together with data from vehicle (DMSO) control, and cells not expressing slc26a3. For screening, the non-selective chloride channel blocker niflumic acid was used as a positive control, which strongly inhibited slc26a3 at 350 μM. The Z'-factor for the slc26a3 screening assay was ~0.7.

To test whether second messengers regulate slc26a3 activity in the transfected FRT cells, experiments were done in which FRT-YFP-slc26a3 cells were pre-incubated with forskolin (20 μM; to elevate cAMP), 8-bromoguanosine 3',5'-cyclic monophosphate (100 μM; 8-Br-cGMP; a cell permeable cGMP analog), ATP (100 μM; to elevate cytoplasmic Ca$^{2+}$), phorbol 12-myristate 13-acetate (100 nM; PMA), or 20 mM potassium chloride (high K+, to depolarize membrane potential). None of these maneuvers significantly altered electroneutral slc26a3-mediated Cl$^-$/I$^-$ exchange (FIG. 1C). Therefore, inhibitors identified in the screen are likely to inhibit slc26a3 exchange directly rather than acting on upstream signaling mechanisms.

Figure 2:
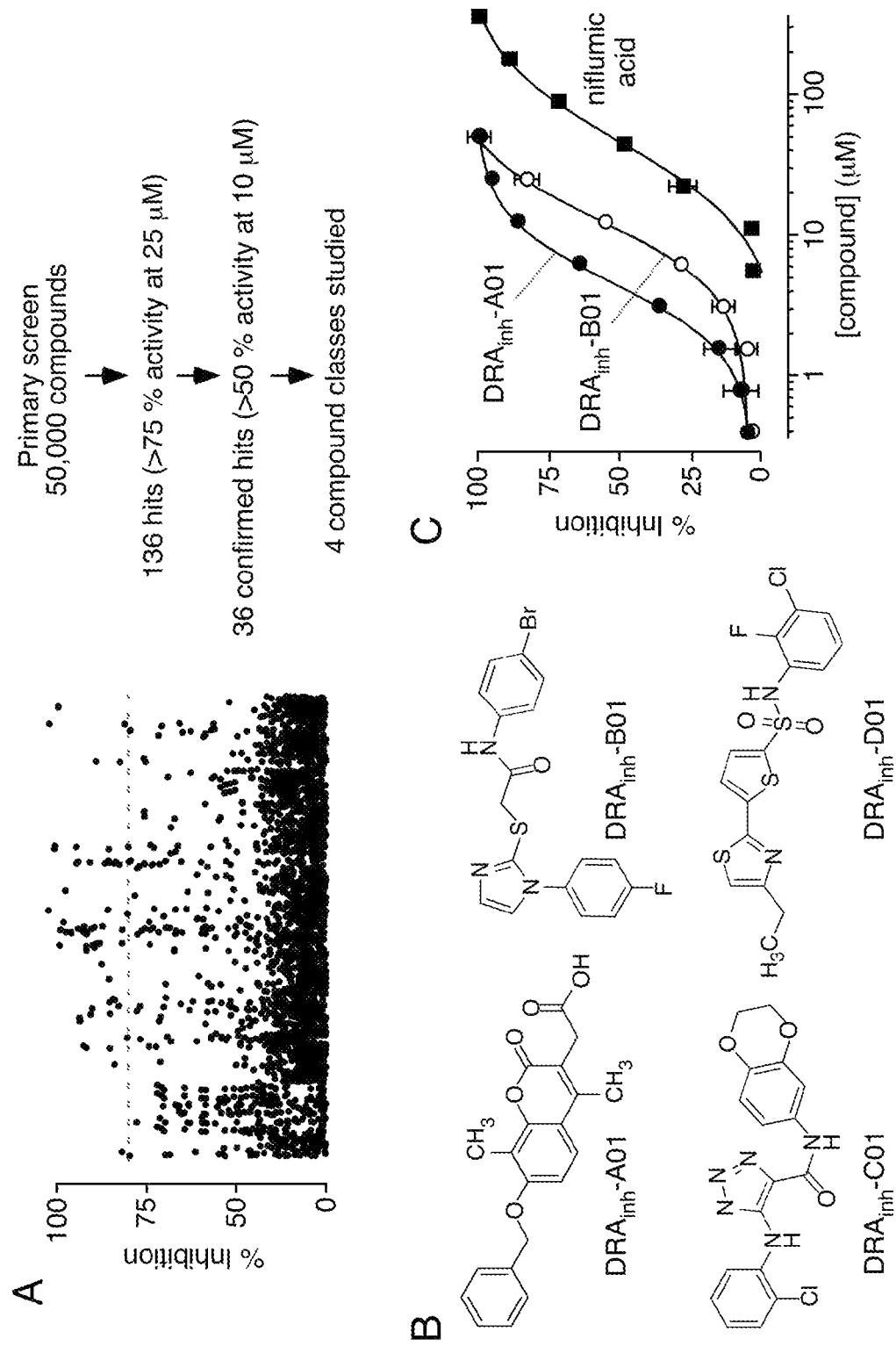
FIG. 2. Murine slc26a3 inhibitors identified by high-throughput screening. A. (left panel) Dot plot of primary screen data for 18,000 compounds at 25 µM showing percentage inhibition, (right panel) summary of results from screen. B. Structures of active compounds of four chemical classes identified in the primary screen. C. Concentration-dependence of slc26a3 inhibition for a Class A and a Class B compound identified in screening, and niflumic acid (mean±S.E.M., n=6). Fitted curves for a single-site inhibition model.

Screening of 50,000 synthetic small molecules at 25 μM identified 136 active compounds that inhibited slc26a3 by >75%. The compounds clustered in several compound classes, including 4,8-dimethylcoumarins, acetamide-thioimidazoles, triazoleamides, and thiazole-thiophenesulphonamides (Classes A-D, respectively) (FIG. 2A-B). A scatter plot of inhibition percentage for a subset of screened compounds, shown in the order as screened (FIG. 2A, left), revealed clusters of active compounds as a consequence of grouping of chemical scaffolds in compound plates. On retesting, 36 compounds inhibited slc26a3 by more than 50% at 10 μM (FIG. 2A, right), including multiple Class A and Class B compounds. FIG. 2C shows concentration-dependence measurements for inhibition of slc26a3-mediated Cl$^-$/I$^-$-exchange for a selected Class A (IC$_{50}$~4 μM) and Class B (IC$_{50}$~9 μM) compound discovered in the primary screen, together with data for niflumic acid (IC$_{50}$~60 μM).

Example 2

Structure-Activity Relationship (SAR) Studies

Figure 3:
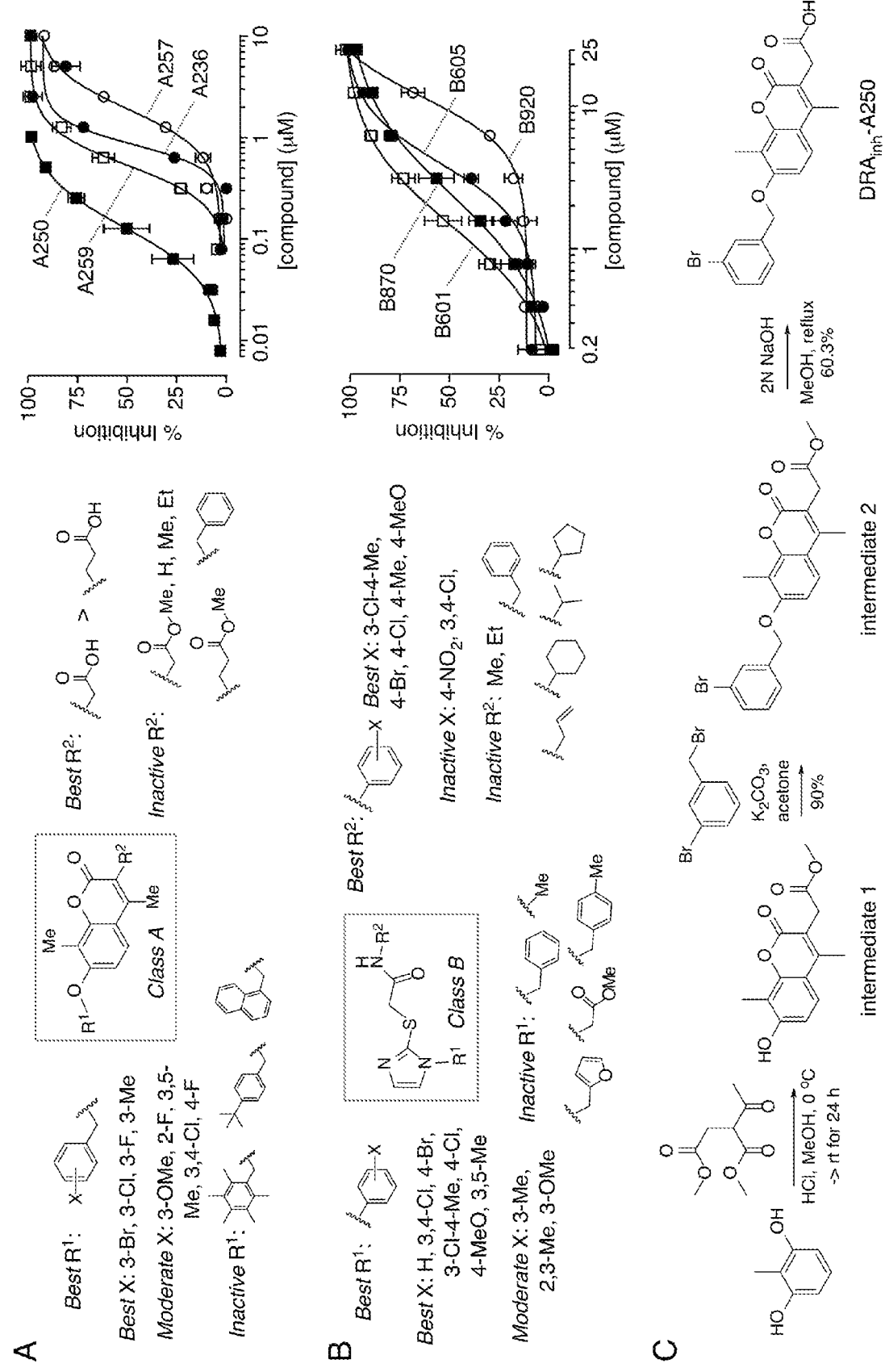
FIG. 3. Structure-activity relationships for Class A and Class B slc26a3 inhibitors. A. Class A. (left panel) Core structure of the Class A inhibitor is boxed; active and inactive substituents are listed. (right panel) Concentration-dependence measurements for selected Class A compounds, including Compound A1 (also referred to as $DRA_{inh}$-A250). B. Class B, showing core structure with active and inactive substituents (left panel) and concentration-dependence measurements (right panel). C. Route for synthesis of Compound A1.

Based on potency data and structural considerations, compounds of Class A and Class B were prioritized for further study. A total of 176 commercially available class A analogs and 175 class B analogs were tested. FIGS. 3A and 3B summarize the structural determinants of activity for Class A and Class B compounds (left panels), with concentration-dependence data of selected analogs provided (right panels). Class A compounds are coumarins that are substituted with methyl group on the 4- and 8-positions. Structure-activity analysis showed that the acetic acid moiety at the 3-position ($R^1$) is beneficial for activity, as the corresponding acetate ester was inactive. Replacement of the acetic acid with propanoic acid greatly reduced activity, and non-acid substituents including alkyl and benzyl were inactive. Greatest potency was found for hydroxylation at the 7-position on the coumarin with a benzyl ring ($R^2$), with 3-chloro, 3-fluoro and 3-bromo substituents giving greatest potency.

Class B compounds are acetamide-thioimidazoles with substituents on the imidazole ($R^1$) ring and acetamide linker ($R^2$). For the $R^1$ group, phenyl gave the best activity, with benzofuran, benzyl, methyl and acetate reducing activity. Unsubstituted phenyl gave the greatest potency although 4-methoxy and 4-chloro were 15 also active, while substituents on the 2-position reduced activity. For $R^2$, several substituted anilines were active, whereas non-aniline, alkyl, benzyl and allyl groups reduced activity. Aniline substituted with 3-chloro-4-methyl were most active. Other substituents on the aniline ring, including 4-halide, 4-methyl and 4-methoxy, were active. In general, 3,4-disubstituted and 3,4-disubstitution reduced activity.

Tables 1 and 2 list $IC_{50}$ values for selected active Class A and Class B compounds, respectively. Compound A1 was the most potent Class A compound with $IC_{50}$ of 0.15 µM (FIG. 3A, right panel). Several other Class A analogs were also found to be more potent than $DRA_{inh}$-A01, the original compound identified in the primary screen. For class B, a number of analogs showed greater potency than the original active compound ($DRA_{inh}$-B01, $IC_{50}$~9 µM), with Compound B1 ($DRA_{inh}$-B601) having lowest the $IC_{50}$ of ~1.5 µM (FIG. 3B, right panel).

4-substituted anilines with electron-neutral or donating groups were best, whereas 4-$NO_2$ and 3,4-disubstitution reduced activity.

TABLE 1

Structures and $IC_{50}$ of selected class A analogs.

| Compound | $R^1$ | $R^2$ | $IC_{50}$ (µM) |
|---|---|---|---|
| A1 | 3-bromo-benzyl |  | 0.15 |
| A2 | 3-chloro-benzyl |  | 0.20 |
| A3 | 3-methyl-benzyl |  | 0.48 |
| A4 | 2-fluoro-benzyl |  | 0.51 |
| A5 | 3,5-dimethyl-benzyl |  | 0.54 |
| A6 | 3-fluoro-benzyl |  | 0.84 |
| A7 | 3,4-dichlorobenzyl |  | 1.8 |
| A8 | 4-tert-butyl-benzyl |  | 4.6 |
| A9 | 2,5-dimethyl-benzyl |  | 4.7 |
| A10 | benzyl |  | 5.1 |
| A11 | 1-(2-methyl-naphthalene) methylene |  | inactive |
| A12 | 4-fluoro-benzyl |  | inactive |
| A13 | 4-tert-butyl-benzyl |  | inactive |
| A14 | 3-methoxy-benzyl |  | inactive |

TABLE 2

Structures and $IC_{50}$ of selected class B analogues

| Compound | $R^1$ | $R^2$ | $IC_{50}$ (µM) |
|---|---|---|---|
| B1 | phenyl | 3-chloro-4-methylphenyl | 1.5 |
| B2 | 4-chlorophenyl | 4-methylphenyl | 1.6 |
| B3 | 4-ethoxyphenyl | 4-chlorophenyl | 1.7 |
| B4 | 4-chlorophenyl | 4-chlorophenyl | 1.7 |
| B5 | 4-chlorophenyl | 4-bromophenyl | 1.8 |
| B6 | 4-methoxyphenyl | 4-bromophenyl | 1.9 |
| B7 | 3,5-dimethylphenyl | 3,4-dichlorophenyl | 2.5 |
| B8 | 3,5-dimethylphenyl | 3-chloro-4-methylphenyl | 2.1 |
| B9 | 3-chlorophenyl | 4-chlorophenyl | 2.2 |
| B10 | 4-fluorophenyl | 3,4-dichlorophenyl | 2.6 |
| B11 | 3-chlorophenyl | 3,4-dichlorophenyl | 2.9 |
| B12 | 2,3-dimethylphenyl | 4-ethylphenyl | 3.5 |
| B13 | 3,5-dimethylphenyl | 4-chlorophenyl | 4.6 |
| B14 | 3-methoxyphenyl | 4-chlorophenyl | 4.7 |
| B15 | 3-chlorophenyl | 4-methylphenyl | 5.1 |
| B16 | 4-chlorophenyl | 4-ethylphenyl | 5.7 |
| B17 | 3-methylphenyl | 4-chlorophenyl | 6.2 |
| B18 | 3-methylphenyl | 4-bromophenyl | 6.4 |
| B19 | 4-methoxyphenyl | 4-ethylphenyl | 6.5 |
| B20 | 3-methoxyphenyl | 4-methylphenyl | 7.1 |
| B21 | 4-chlorophenyl | 4-nitrophenyl | 7.4 |
| B22 | 4-chlorophenyl | 3-chloro-4-methylphenyl | 11 |
| B23 | 4-chlorophenyl | 3-trifluoromethylphenyl | 12 |

Example 3

Synthesis of Compound A1 ($DRA_{INH}$-A250)

For further studies Compound A1 was resynthesized (FIG. 3C) by Pechmann condensation of 2-methylresorcinol with dimethyl acetylsuccinate to yield 7-hydroxycoumarin (intermediate 1), which was further alkylated with 3-bromobenzyl bromide to give coumarin ester (intermediate 2). Hydrolysis of the coumarin ester gave the corresponding 3-acetic acid-coumarin Compound A1 in good yield (FIG. 3C).

2-methylresorcinol (2.00 g, 16.09 mmol) and dimethyl 2-acetylsuccinate (3.03 g, 16.1 mmol) in absolute methanol (40 mL) were treated with dry HCl at 0° C. The reaction mixture was then stirred at room temperature for 24 h, and the mixture was poured into water. The resulting precipitate was collected by filtration, washed with water, and dried to give an off-white solid (3.02 g, 72% yield) of the desired product (intermediate 1). $^1$H NMR (300 MHz, MeOH-d4) δ 7.51 (dd, J=8.7, 0.45 Hz, 1H), 6.86 (d, J=8.7 Hz, 1H), 3.728 (s, 2H), 3.720 (s, 3H), 2.41 (s, 3H), 2.27 (s, 3H); LC/MS m/z 262 (M+H+).

A mixture of 7-hydroxycoumarin (intermediate 1) (200 mg, 0.76 mmol), 3-bromobenzyl bromide (267 mg, 1.07 mmol), and potassium carbonate (211 mg, 1.53 mmol) in acetone (10 mL) was heated to reflux overnight. The solvent was evaporated and the residue poured into ice water. The resulting precipitate was collected by filtration, washed with methanol, and dried to give 290 mg (90%) of coumarin ester (intermediate 2) as white solid. $^1$H NMR (300 MHz, CDCl3) δ 7.61 (brs, 1H), 7.51-7.48 (m, 1H), 7.46 (d, 1H, J=8.9 Hz), 7.39 (d, 1H, J=8.0 Hz), 7.29 (t, 1H, J=7.8 Hz), 6.87 (d, 1H, J=8.9 Hz), 3.75 (brs, 2H), 3.73 (s, 3H), 2.39 (brs, 6H); $^{13}$C NMR (75 MHz, CDCl3) δ 170.9, 161.8, 158.6, 151.6, 149.0, 138.8, 131.2, 130.2, 130.0, 125.5, 122.76, 122.72, 116.5, 114.5, 114.4, 108.1, 69.5, 52.2, 32.7, 15.3, 8.4; LC/MS m/z 431 (M+H+).

To a solution of the ester intermediate 2 (180 mg, 0.42 mmol) in methanol (8 mL) was added NaOH (25 mg, 0.626 mmol) in water (2 mL) and the solution was heated to reflux for 1 h, cooled to room temperature, diluted with water and neutralized to pH 7.0 with 1N HCl. The resulting precipitate was collected by filtration, washed with water and dried to give Compound A1 as a white powder (105 mg, 60% yield). $^1$H NMR (300 MHz, DMSO-d6) δ 7.73 (brs, 1H), 7.66 (d, 1H, J=9.1 Hz), 7.57-7.54 (m, 2H), 7.42-7.37 (m, 1H), 7.13 (d, 1H, J=8.9 Hz), 5.34 (s, 2H), 3.73 (s, 2H), 2.45 (s, 3H), 2.33 (s, 3H); $^{13}$C NMR (75 MHz, DMSO-d6) δ 165.8, 161.4, 158.4, 151.1, 149.1, 144.1, 140.1, 131.2, 130.4, 126.7, 124.0, 122.2, 117.8, 114.4, 112.9, 109.2, 69.3, 33.6, 15.5, 8.5; LC/MS m/z 417 (M+H+).

Example 4

Compound A1 Characterization

Figure 4:
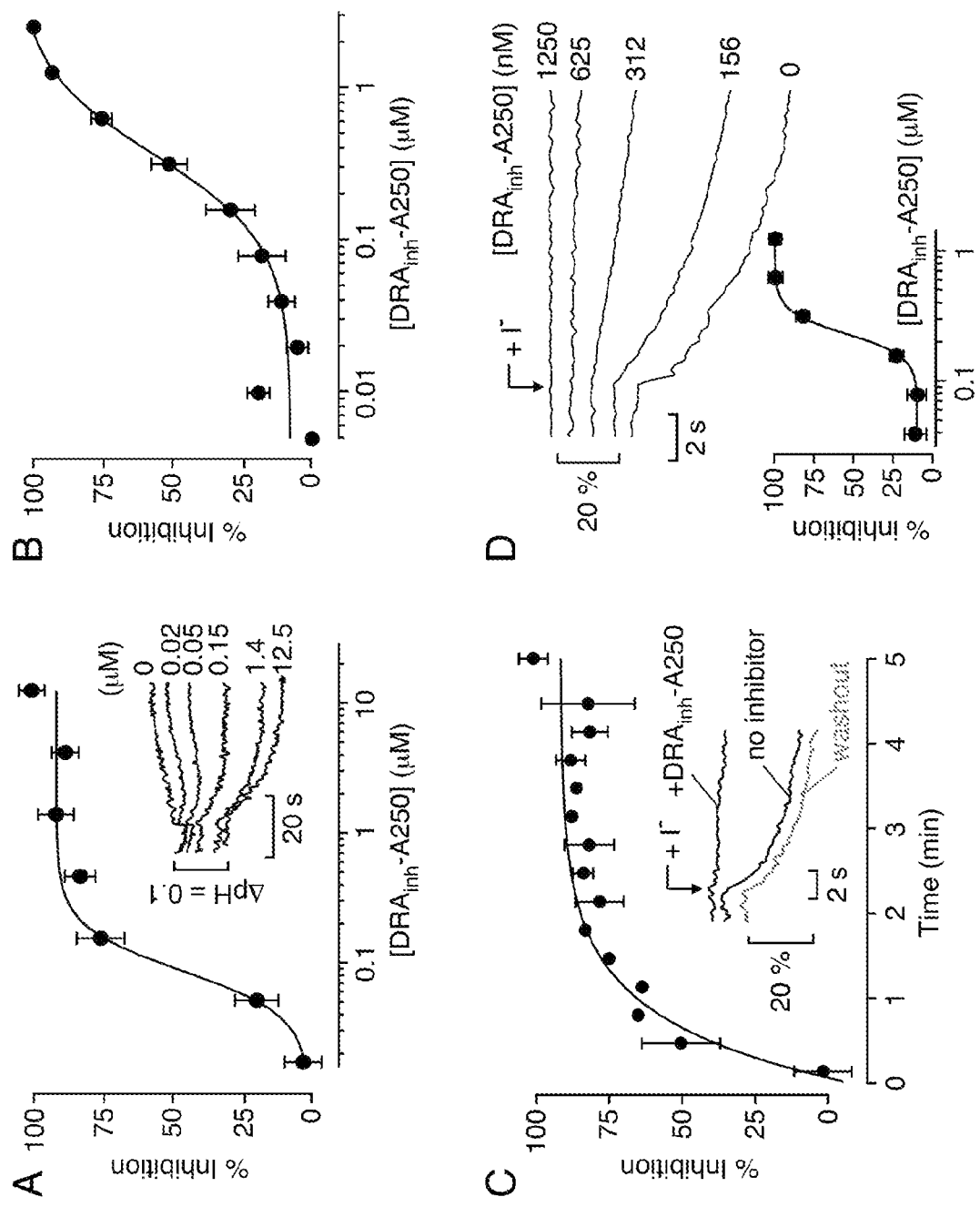
FIG. 4. Characterization of Compound A1 action. A. Concentration-dependence of Compound A1 inhibition of slc26a3-mediated $Cl^-/HCO_3^-$ exchange (mean±S.E.M., n=6). (inset) Original BCECF fluorescence curves for $Cl^-/HCO_3^-$ exchange. B. Concentration-dependence of Compound A1 inhibition of slc26a3-mediated $Cl^-/SCN^-$ exchange (mean±S.E.M., n=6). C. Time course of Compound A1 (1 µM) inhibition of slc26a3-mediated $Cl^-/I^-$ exchange (mean±S.E.M., n=4). (inset) Reversibility of Compound A1 (1 µM) inhibition of slc26a3-mediated $Cl^-/I^-$ exchange (mean±S.E.M., n=4). D. Inhibition of (human) SLC26A3-mediated $Cl^-/I^-$ exchange in HEK cells. YFP fluorescence traces (top) and summary data (mean±S.E.M., n=12-26 individual cells analyzed) (inset).

Concentration-dependence measurements for inhibition of slc26a3-mediated exchange of Cl$^-$ and HCO$_3^-$, the physiologically relevant activity of slc26a3, was measured using slc26a3-expressing FRT cells labeled with BCECF as a cytoplasmic pH sensor. Labeled cells were initially incubated in a Cl$^-$-containing HCO$_3^-$ buffered solution, and HCO$_3^-$ influx/Cl efflux with cytoplasmic alkalinization was produced by addition of a gluconate-containing HCO$_3^-$ buffered solution. The increase in cytoplasmic pH (~0.05 pH units/min) was inhibited by Compound A1 with IC$_{50}$~0.1 μM (FIG. 4A). Concentration-dependence measurements for inhibition of slc26a3-mediated Cl$^-$/SCN$^-$ exchange gave an IC$_{50}$ of ~0.3 μM (FIG. 4B). The kinetics of Compound A1 inhibition, measured by incubation of FRT-YFP-slc26a3 cells with 1 μM Compound A1 for different times prior to initiation of Cl$^-$/I$^-$ exchange, showed a t$_{1/2}$ for inhibition of ~30 s (FIG. 4C). To confirm full reversibility, FRT-YFP-slc26a3 cells were incubated with 1 μM Compound A1 for 10 min and then washed three times prior to assay Cl$^-$/I$^-$ exchange (FIG. 4C, inset).

Inhibition of (human) SLC26A3 by Compound A1 was also tested, using a HEK cell model expressing SLC26A3 and YFP. SLC26A3-mediated Cl$^-$/I$^-$ exchange was inhibited by Compound A1 with IC$_{50}$~0.25 μM with complete inhibition at higher Compound A1 concentrations (FIG. 4D).

Example 5

Compound A1 Selectivity

Figure 5:
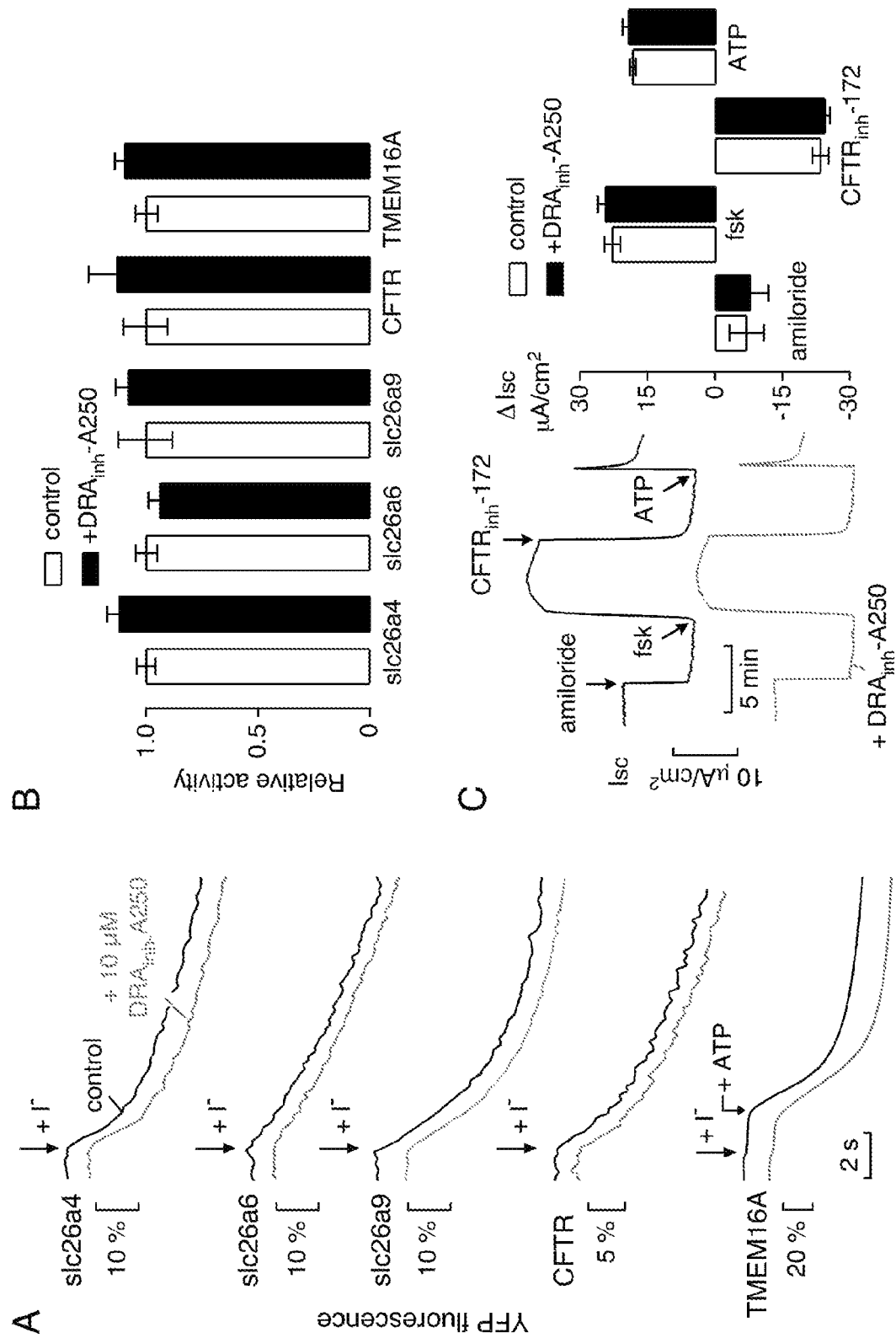
FIG. 5. Compound A1 selectivity. A. Time course of YFP fluorescence in $Cl^-/I^-$-exchange assays for pendrin (slc26a4), PAT-1 (slc26a6), slc26a9, CFTR (forskolin stimulated), and TMEM16A (ATP-stimulated) in the absence (black traces) and presence (grey traces) of 10 µM Compound A1. B. Summary data for studies as in panel A with data normalized to control conditions (white bars) (mean±S.E.M., n=4 for plate reader assays, and n=14-29 for single cell assays, differences not significant). C. (left panel) Short-circuit current ($I_{sc}$) in well-differentiated HBE cells grown at an air-liquid interface. Studies done in the absence (black traces) and presence (grey traces) of 10 µM Compound A1. Where indicated, amiloride (20 µM), forskolin (20 µM), $CFTR_{inh}$-172 (10 µM) and ATP (100 µM) were added. (right panel) Changes in $I_{sc}$ for modulator additions (mean±S.E.M., n=3, differences not significant).

To investigate Compound A1 selectivity, transport assays were done on a panel of SLC26-family homologs, and other relevant epithelial ion transporters and channels. Pre-incubation of cells with Compound A1 at 10 μM did not alter Cl$^-$/I$^-$-exchange activity of (murine) pendrin (slc26a4), PAT-1 (slc26a6) or slc26a9, as shown in original fluorescence time course data (FIG. 5A) and summary data (FIG. 5B). Compound A1 at 10 μM also did not alter the activity of the Cl$^-$ channels CFTR and TMEM16A. In separate studies, to investigate possible action of Compound A1 on multiple ion transporters and channels in a human epithelium, human bronchial epithelial (HBE) cells were studied by short-circuit current, with successive additions of amiloride (to block the epithelial sodium channel ENaC), forskolin, CFTR$_{inh}$-172 (to block CFTR), and ATP (to activate the Ca$^{2+}$-activated chloride channel, CaCC) (FIG. 5C). Pre-treatment for 20 min with 10 μM Compound A1 did not alter short-circuit current responses, indicating that Compound A1 did not affect ENaC, CFTR or CaCC activity, or the activity of other transporters, including K$^+$ channels and the Na—K—Cl co-transporter NKCC1, that are required to support their activity.

Example 6

Closed Loop Studies

Female CD1 mice (age 8-10 weeks) were given free access to Pedialyte (per liter: Na$^+$ 45 mEq, Cl$^-$ 35 mEq, K$^+$ 20 mEq, dextrose 25 g; Abbott, Abbot Park, Ill.) but not solid food for 48 h before experiments. Mice were treated with 500 μL mineral oil once a day rectally (last dose 12 h before surgeries) during this period to evacuate the colon. Closed intestinal loops were isolated as described. Mice were anesthetized with isoflurane and body temperature was maintained during surgery at 36-38° C. using a heating pad. A small abdominal incision was made to expose the distal colon, and one closed distal colonic loop (length 1.5-2 cm) was isolated with sutures in each mouse. Loops were injected with 100 μL phosphate-buffered saline (PBS, pH: 7.4, in mM: 137 NaCl, 2.7 KCl, 8 Na$_2$HPO$_4$, 1.8 KH$_2$PO$_4$, 1 CaCl$_2$, 0.5 MgCl$_2$) without and with 10 μM Compound A1 and/or 10 μM tenapanor (Med Chem Express, Monmouth Junction, N.J.). The abdominal incision was closed with sutures, and mice were allowed to recover from anesthesia. Colonic loops were removed at 0 and 60 min (in separate mice) and loop length and weight were measured to quantify fluid absorption. Luminal fluid was emptied with a syringe and pH was measured immediately using AB15 pH Meter (Thermo Fisher Scientific, South San Francisco, Calif.). In separate studies, mid-jejunal loops (length 2-3 cm, 3-4 loops per mouse) were isolated as described above, injected with 100 μL PBS without or with 10 μM Compound A1 and/or 10 μM tenapanor, and excised at 0 and 30 min to measure loop length and weight.

Example 7

Inhibition of Fluid Absorption in Distal Colon of Mice

Figure 6:
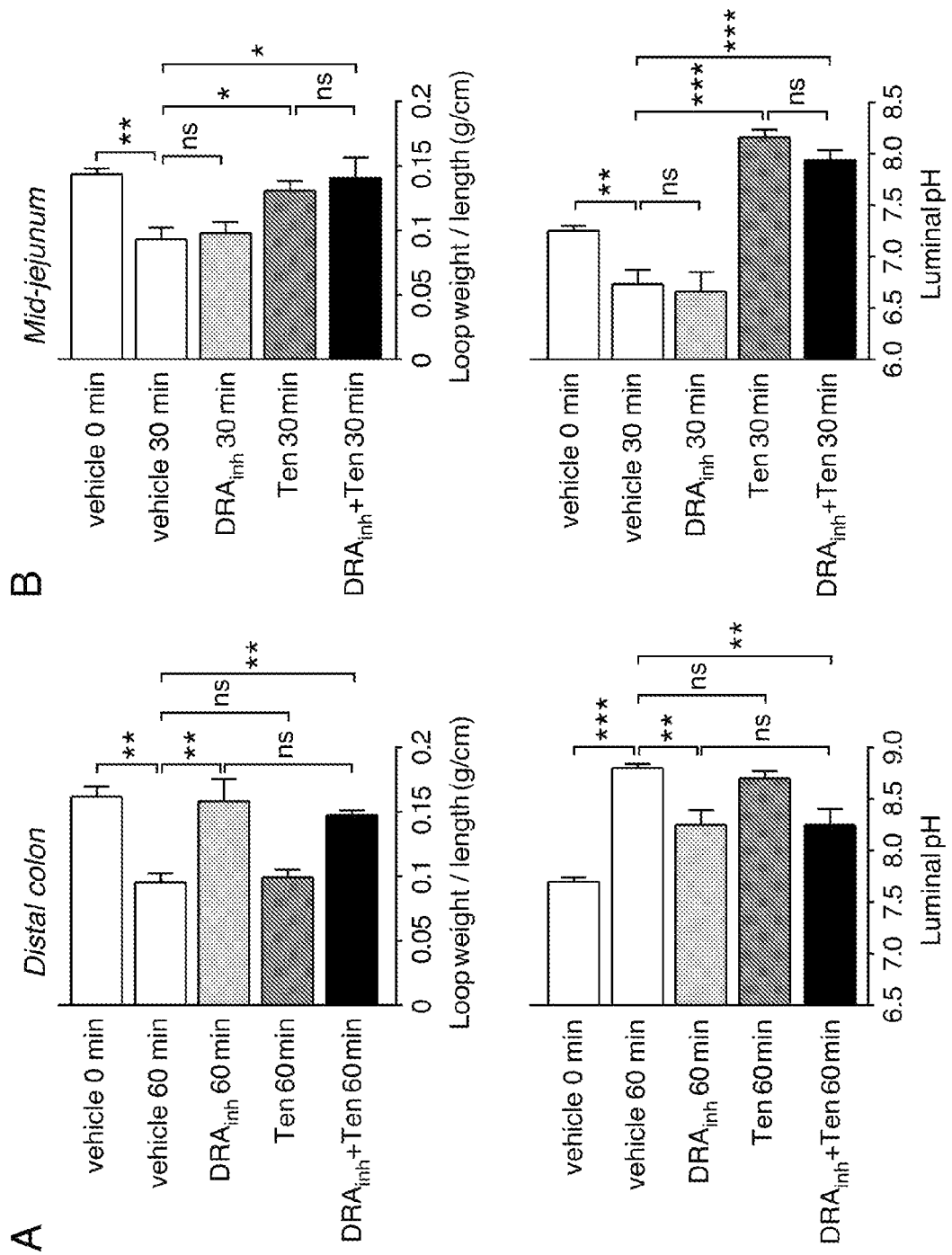
FIG. 6. Compound A1 inhibits intestinal fluid absorption in mouse distal colon but not in jejunum. A. Effects of Compound A1 (10 µM) and tenapanor (10 µM), individually and together, on loop weight/length ratio (top) and luminal pH (bottom) in mouse distal colonic closed loops (mean±S.E.M., n=4 loops per group). B. Effects of Compound A1 (10 µM) and tenapanor (10 µM), individually and together, on loop weight/length ratio (top) and luminal pH (bottom) in mouse mid-jejunal closed loops (mean±S.E.M., n=5-9 loops per group). *P<0.05, P<0.01, *P<0.001, ns: not significant, one-way analysis of variance with post-hoc Newman-Keuls multiple comparisons test. $DRA_{inh}$: Compound A1, Ten: tenapanor.

Closed intestinal loop studies in mice were done to study effects of Compound A1 on fluid absorption. Compound A1 administration directly in isolated distal colonic loops completely prevented the reduction in loop weight/length ratio at 60 min, a direct measure of fluid absorption (FIG. 6A, top panel). Changes in luminal pH were also determined as a semi-quantitative measure of slc26a3-facilitated HCO$_3^-$ secretion/Cl$^-$ absorption, with slc26a3 inhibition predicted to reduce luminal fluid alkalinization. For these experiments, a phosphate-buffered solution (PBS) without $HCO_3^-/CO_2$ was used to avoid confounding effects of luminal carbonic anhydrases. Compound A1 reduced alkalinization of luminal fluid in the distal colonic loops at 60 min, consistent with inhibition of $Cl^-/HCO_3^-$ exchange (FIG. 6A, bottom panel). Administration of the NHE3 ($Na^+/H^+$ exchanger 3) inhibitor tenapanor had no effect on weight/length ratio or luminal pH in distal colonic loops. Results with co-administration of Compound A1 and tenapanor were similar to those with Compound A1 alone. These results support the conclusion that slc26a3 is the predominant pro-absorptive transporter in mouse distal colon, whereas NHE3 does not contribute significantly to fluid absorption in this segment.

Example 8

Jejunal Fluid Absorption Unaltered by Slc26a3 Inhibition

Administration of Compound A1 to mid-jejunal loops did not produce significant changes in loop weight/length ratio, whereas fluid absorption was abolished in tenapanor-treated loops (FIG. 6B, top panel). Compound A1 did not alter acidification of jejunal fluid at 30 min, with tenapanor preventing acidification and producing slight alkalinization (FIG. 6B, bottom panel). Loops co-administered Compound A1 and tenapanor showed loop weight/length ratio and luminal fluid pH that were similar to treatment with tenapanor alone. These results provide evidence against a significant role of slc26a3 in fluid absorption in mouse jejunum, and support the conclusion that NHE3 is a predominant pro-absorptive transporter in this segment.

Example 9

Reduction of Loperamide-Induced Constipation in WT and Cystic Fibrosis Mice

Female CD1 mice (age 8-10 weeks) were administered loperamide (0.3 mg/kg, intraperitoneally, Sigma-Aldrich) to produce constipation. Compound A1 (DRAinh-A250) (5 mg/kg, in saline containing vehicle (5% DMSO and 10% Kolliphor HS 15; Sigma-Aldrich)), tenapanor (5 mg/kg, in vehicle), or both compounds (5 mg/kg each, in vehicle), or vehicle alone were administered by oral gavage 1 hour before loperamide. After loperamide injection, mice were placed individually in metabolic cages with ad libitum access to food and water. Stool samples were collected for 3 h, and total stool weight and number of fecal pellets were quantified. To measure stool water content, stool samples were dried at 80° C. for 24 h and water content was calculated as [wet weight-dry weight]/wet weight. Similar studies were done in cystic fibrosis (CF) mice (ΔF508 homozygous) lacking functional CFTR.

Figure 7:
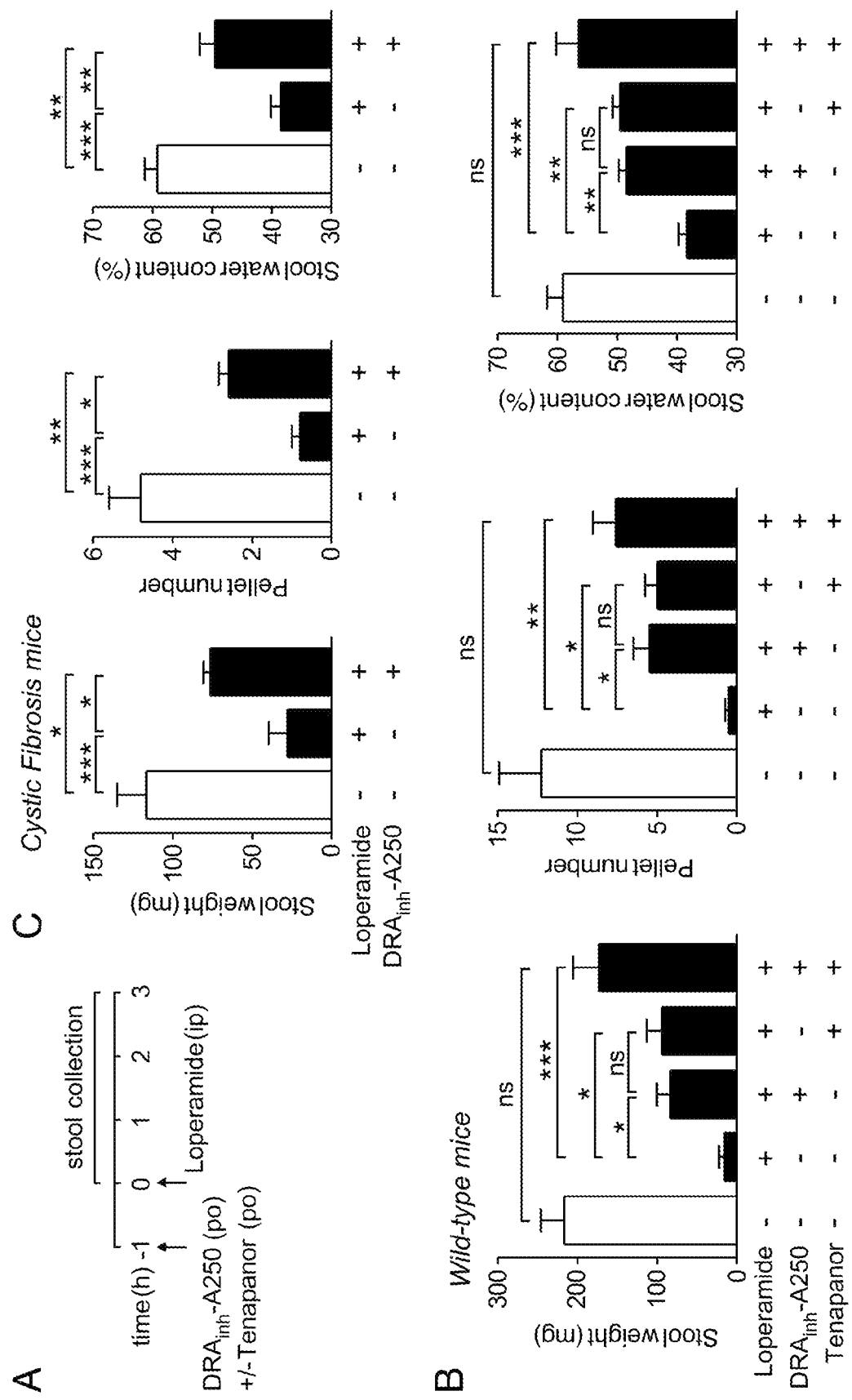
FIG. 7. Oral Compound A1 reduces loperamide-induced constipation in wild-type and cystic fibrosis mice. A. Mouse model of constipation produced by loperamide. B. Effects of Compound A1 (5 mg/kg) and tenapanor (5 mg/kg), individually and together, on three-hour stool weight, number of pellets, and stool water content in loperamide-treated wild-type mice (mean±S.E.M., n=5-7 mice per group) with vehicle control shown for comparison. C. Study as in panel A done in cystic fibrosis mice lacking functional CFTR (means S.E.M., n=5 mice per group). *P<0.05, P<0.01, *P<0.001, ns: not significant; one-way analysis of variance with post-hoc Newman-Keuls multiple comparisons test.

Orally administered Compound A1 at 5 mg/kg partially prevented the loperamide-induced reduction in stool weight, pellet number and water content in wild-type mice (FIGS. 7A and 7B). Tenapanor given orally at 5 mg/kg also partially prevented loperamide-induced reduction in stool weight, pellet number and water content. The magnitude of these responses is similar to that seen with very high doses of the approved drug linaclotide. Remarkably, co-administration Compound A1 and tenapanor completely prevented loperamide-induced constipation, suggesting an additive effect of slc26a3 and NHE3 inhibition on stool hydration (FIG. 7B). Importantly, Compound A1 was also effective in a loperamide-induced constipation model in CF mice having loss of function of the pro-secretory $Cl^-$ channel CFTR (FIG. 7C).

Figure 8:
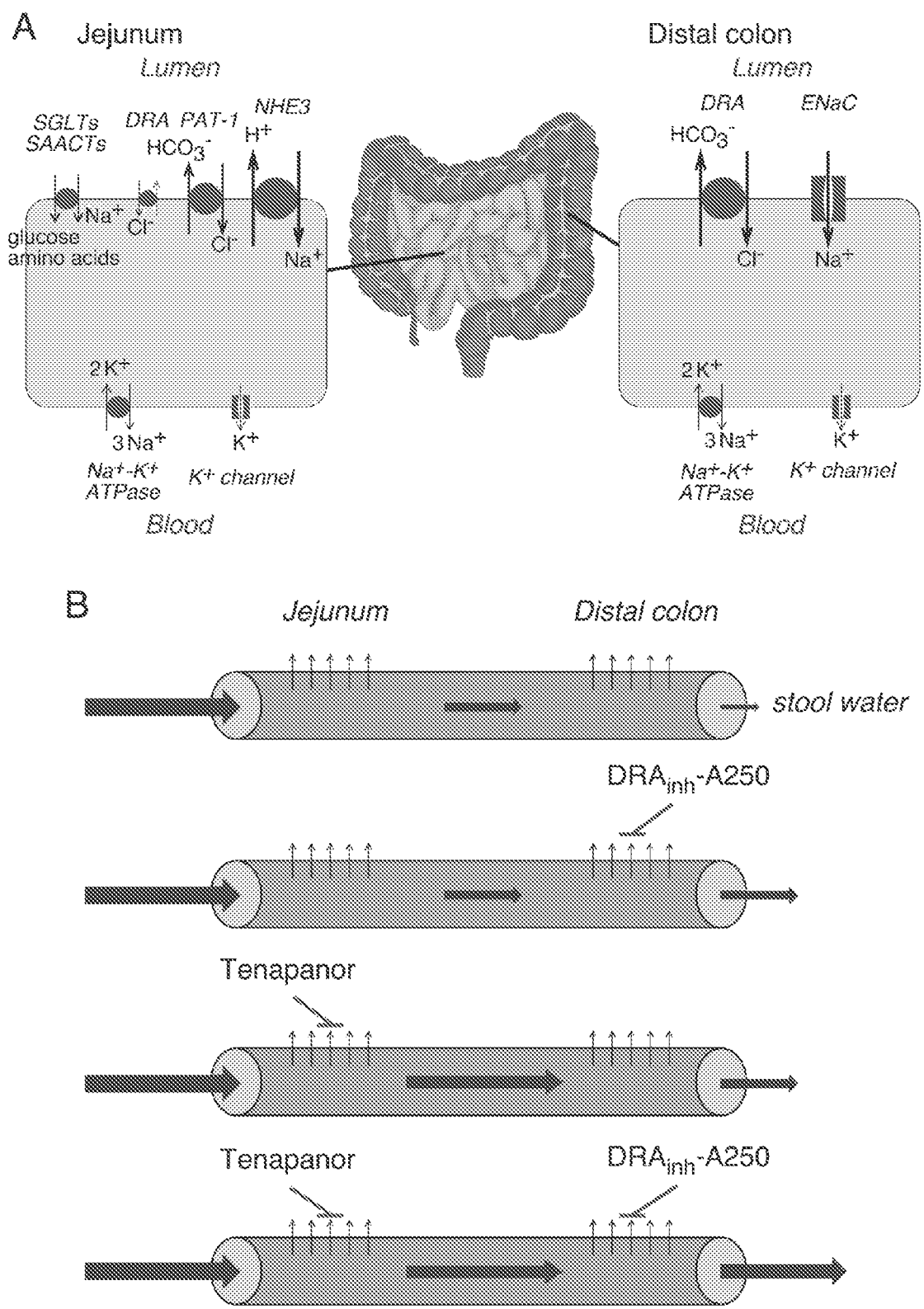
FIG. 8. A. Absorptive mechanisms in jejunum and distal colon. Arrow size denotes relative importance in fluid absorption. B. Proposed sites of actions and mechanism for Compound A1 and tenapanor.

FIG. 8 (A and B) illustrate schematically the possible mechanisms underlying the observed results. FIG. 8A diagrams the major absorptive pathways in jejunum and distal colon. NHE3 and NHE2 are expressed in small intestine and proximal colon; NHE3 (SLC9A3) is the dominant $Na^+/H^+$ exchanger as it can compensate for loss of NHE2. The notations have the following meanings: DRA: down-regulated in adenoma (Slc26a3), PAT-1: putative anion transporter-1 (Slc26a6), NHE3: $Na^+/H^+$ exchanger 3, ENaC: epithelial sodium channel. SGLTs: $Na^+$-glucose transporters, SAACTs: $Na^+$-amino acid cotransporters.

FIG. 8B shows the possible sites of actions and mechanism for Compound A1 and tenapanor. Upward vertical arrows represent absorption, size and thickness of the horizontal arrows represent hydration of luminal content and stool output.

Example 10

Vector Expression

Vectors containing complementary DNA (cDNA) for slc26a3, SLC26A3, slc26a6, and slc26a9 were purchased from Origene (Rockville, Md.) and manipulated using standard techniques. To generate a cell line for screening, slc26a3 was subcloned into pIRESpuro3 (Clontech, Mountain View, Calif.). Human SLC26A3 was subcloned into pLVX-IRES-mCherry (Clontech) and other slc26 family members were subcloned into vectors that were generated to co-express the halide sensitive EYFP-H148Q/I152L/F46L (YFP).

Specifically, to generate slc26a3 expression vector, a KpnI-EcoRI fragment excised from the Origene plasmid (containing the start codon and ~1.7 kb of the coding sequence) and a synthetic DNA fragment (gBLOCK, Integrated DNA Technologies (Coralville, Iowa), ~0.6 kb) encoding the carboxy-terminal slc26a3 region, and 5'-EcoRI/3'-BstXI/XhoI restriction sites, were used to regenerate slc26a3 in pcDNA3.1/zeo(+) (Thermo Fisher Scientific, South San Francisco, Calif.). Subsequently, slc26a3 cDNA, excised with BglII and BstXI, was subconed into BamHI and BstXI sites of pIRESpuro3 (Clontech, Mountain View, Calif.).

For SLC26A3, a KpnI-PstI fragment excised from the Origene plasmid (containing the start codon and ~1.9 kb of the coding sequence) and a ~0.6 kb gBLOCK encoding the carboxy-terminal SLC26A3 region, and 5'-PstI and 3'-NotI restriction sites, were used to regenerate SLC26A3 in pcDNA3.1/zeo(+). Subsequently, SLC26A3 cDNA, excised with NheI and NotI, was subcloned into the SpeI and NotI sites of pLVX-IRES-mCherry (Clontech).

To generate a plasmid for co-expression of slc26a9 and halide sensitive EYFP-H148Q/I152L/F46L (YFP), pIRESpuro3 was digested with ApaI and XmaI and regenerated with a gBLOCK that replaced the puromycin resistance gene ($Puro^r$) with YFP, with the resultant vector termed pIRES-YFP. Subsequently, slc26a9 was cloned into pIRES-YFP as an EcoRI-NotI fragment. To generate a lentiviral vector to co-express slc26a6 and YFP, gBLOCKs were used to regenerate pLVX-Puro (Clontech) with YFP-T2A coding sequence inserted upstream of, and in frame with the $Puro^r$, with the resultant vector termed pLVX-YFP-T2A-Puro. A KpnI-PstI fragment was excised from the Origene slc26a6 plasmid (containing ~2 kb of the 3'-region) and a ~0.5 kb gBLOCK encoding the amino-terminal slc26a6 cDNA region with start codon, and 5'-NheI/EcoRI and 3'-KpnI restriction sites, were used to regenerate slc26a6 in pcDNA3.1/zeo(+). Subsequently, full-length slc26a6 was subcloned into pLVX-YFP-T2A-Puro as an EcoRI to XbaI fragment. All constructs were confirmed by sequencing.

Example 11

Cell Culture and Transfection

Fischer rat thyroid (FRT) epithelial cells, HEK cells and human bronchial epithelial cell cultures were cultured using standard methods known in the art. For slc26a3 inhibitor screening, an FRT cell line virally transduced to express YFP was transfected with pIRESpuro3-slc26a3, selected using 0.15 µg/ml puromycin, and a clonal cell line (termed FRT-YFP-slc26a3) was isolated. Specifically, Fischer rat thyroid (FRT) cells were cultured in Kaign's modified Ham's F12 medium supplemented with 10% FBS, 2 mM L-glutamine, 100 U/mL penicillin, 100 µg/mL streptomycin, 18 µg/mL myo-inositol and 45 µg/mL ascorbic acid using techniques known in the art.

For screening to identify slc26a3 inhibitors, FRT cells expressing YFP, generated using the FELIX third generation feline immunodeficiency lentiviral system available from Addgene (deposited by Garry Nolan, plasmid #1728), were transfected with pIRESpuro3-slc26a3 using Lipofectamine 2000 (Thermo Fisher Scientific, South San Francisco, Calif.), selected using 0.15 mg/mL puromycin, and a clonal cell line (termed FRT-YFP-slc26a3) was isolated by functional assessment using a $Cl^-/I^-$-exchange protocol with YFP quenching as readout.

FRT cells expressing YFP and slc26a4 (pendrin) or CFTR are known in the art. HEK293T cells were cultured in DMEM containing 4.5 g/L glucose, 0.11 g/L sodium pyruvate, 0.584 g/L glutamine, 10% FBS, 100 U/mL penicillin, and 100 µg/mL streptomycin, and transfected using NanoFect transfection reagent (Alstem, Richmond, Calif.) per manufacturer's instructions. FRT cells were transfected with Lipofectamine 2000 (Thermo Fisher Scientific, South San Francisco, Calif.) and HEK cells were transfected with NanoFect (Alstem, Richmond, Calif.).

To generate a cell line enriched for expression of SLC26A3, HEK293 cells were transduced with lentiviral particles generated with the pLVX-IRES-mCherry-SLC26A3 transfer vector and then transfected to express YFP.

To generate a cell line enriched for expression of slc26a6 and YFP, HEK293 cells were infected with lentiviral particles generated with the pLVX-YFP-T2A-Puro-slc26a6 transfer vector, and selected with 0.2 mg/mL puromycin. Human immunodeficiency virus-based lentiviral particles were generated using standard procedures in HEK293 cells with the pMD2.G, pRSV-Rev, and pMDLg/pRRE packaging vectors available from Addgene (deposited by Didier Trono, plasmids #12251, #12253, and #12259). Well-differentiated human bronchial epithelial (HBE) cells grown at an air-liquid interface were cultured using techniques known in the art.

Example 12

Selectivity Studies

YFP-based assays of CFTR, pendrin and TMEM16A were as described. HEK cells transfected to express YFP and SLC26A3, slc26a6 or slc26a9 were functionally assayed using a $Cl^-/I^-$ exchange protocol. Assays of $Cl^-/HCO_3^-$ exchange were done using BCECF as an intracellular pH indicator as described for pendrin. Short-circuit current ($I_{SC}$) measurements in well-differentiated HBE cell cultures were done using techniques known in the art.

HEK293 cells transfected with pIRES-YFP-slc26a9 were plated in 96-well black-walled, clear-bottom tissue culture plates (Corning Life Sciences, Tewksbury, Mass.) after coating with FNC Coating Mix (AthenaES, Baltimore, Md.). After washing two-times with PBS and incubating for 10 min in 100 µL PBS containing 10 µM Compound A1, cells were transferred to the stage of a TE2000 microscope (Nikon, Melville, N.Y.) equipped with a C9100 EM-CCD (Hamamatsu, Campbell, Calif.), Nikon 20×N.A. 0.75 S Fluor objective, and B-2E/C and 31002 filter sets (Chroma, Bellows Falls, Vt.) for imaging of green and red emitting fluorophores, respectively. Assays of slc26a9-mediated anion exchange were done by initially recording YFP fluorescence prior to addition of 100 µL of NaI-substituted PBS to test wells, with the initial rate of $Cl^-/I^-$ exchange deduced from fluorescence intensity by single exponential regression. Assays of slc26a6 activity were done in a similar manner using HEK cells transduced with lentiviral particles generated from the pLVX-YFP-T2A-Puro-slc26a6 vector. To assay SLC26A3 function, HEK293 cells transduced with lentiviral particles generated from the pLVX-IRES-mCherry-SLC26A3 transfer vector were transfected to express YFP for $Cl^-/I^-$ exchange assays as described above; red fluorescence images were acquired to confirm SLC26A3 expression in cells. CFTR function, pendrin-mediated $Cl^-/I^-$ exchange, and TMEM16A activity were assayed using techniques known in the art. Short-circuit current ($I_{SC}$) measurements in well-differentiated HBE cell cultures were also done to assess compound selectivity. HBE cells were cultured at an air-liquid interface on Costar Snapwell clear permeable supports (12 mm diameter, 0.4 µm polyester membrane; Corning Life Sciences, Tewksbury, Mass.) and short-circuit current was measured using symmetrical $HCO_3^-$-buffered solutions (in mM: 120 NaCl, 5 KCl, 1 $MgCl_2$, 1 $CaCl_2$, 5 Hepes, 25 $NaHCO_3$; pH 7.4; 95% $O_2$/5% $CO_2$ equilibration; 37° C.) with ion transport modulators added to both apical and basolateral bathing solutions using techniques known in the art.

In summary, it has been found that certain embodiments of compositions comprising a compound of Formula I (e.g., Compound A1) fully and reversibly inhibited slc26a3-mediated $Cl^-$ exchange with $HCO_3^-$, $I^-$ and $SCN^-$ with $IC_{50}$~0.2 µM. At 10 µM, Compound A1 did not inhibit the homologous anion exchangers slc26a4 (pendrin) or slc26a6 (PAT-1), nor did it alter activity of other related proteins or intestinal ion channels. In mice, intraluminal Compound A1 blocked fluid absorption in closed colonic loops but not in jejunal loops, while the NHE3/SLC9A3 inhibitor tenapanor blocked absorption in jejunal but not in colonic loops. Oral Compound A1 and tenapanor comparably reduced signs of constipation in loperamide-treated mice, with additive effects found on co-administration. Compound A1 was also effective in loperamide-treated cystic fibrosis mice.

These studies support a major role of SLC26A3 in colonic fluid absorption and suggest the therapeutic utility of SLC26A3 inhibition in constipation, including constipation associated with cystic fibrosis.

Example 13

SAR Study of Additional DRA Inhibitor Analogs

For further SAR analysis, various substituted benzyl analogs at 7-hydroxy position were synthesized according to Reaction Scheme 1.

TABLE 3

Inhibition activities of representative Class A compounds.

[Structure: 7-RO-8-methyl-4-methyl-coumarin-3-yl-CH2-CO2H]

| Compound | R | IC$_{50}$ (µM) |
|---|---|---|
| A1 (DRAinh-A250) | 3-Br-benzyl | 0.15 |
| A251 | 4-Br-benzyl | N.A. |
| A252 | 2-Br-benzyl | N.A. |
| A253 | 3-NO$_2$-benzyl | 0.5 |
| A2 | 3-Cl-benzyl | 0.20 |
| A5 | 3,5-diMe-benzyl | 0.54 |
| A4 | 2-F-benzyl | 0.51 |
| A7 | 3,4-diCl-benzyl | 1.8 |
| A258 | 2-MeO-benzyl | N.A |
| A3 | 3-Me-benzyl | 0.48 |
| A260 | 3-CF$_3$-benzyl | 0.025 |
| A261 | 3-cyclopropyl benzyl | 0.07 |
| A262 | 3-MeO-benzyl | N.A. |
| A263 | 3,5-diCF$_3$-benzyl | 15 |
| A264 | 2-Cl, 5-F-benzyl | N.A. |
| A265 | [3-CF$_3$-phenyl-CH$_2$CH$_2$-] | N.A |
| A266 | 2-F, 5-CF$_3$-benzyl | 0.1 |
| A267 | 3-F, 5-CF$_3$-benzyl | N.A. |
| A268 | p-I-benzyl | N.A. |
| A269 | o-I-benzyl | 4.5 |
| DRAinh-A270 | m-I-benzyl | 0.04 |
| A271 | [allyl-CH2-] | N.A. |
| A272 | [MeO-CH2-] | N.A. |
| A273 | [HOOC-CH2-] | N.A. |
| A274 | [propyl] | N.A. |
| A275 | [isobutyl/neopentyl] | N.A |
| A276 | [n-pentyl] | 1.5 |
| A277 | [n-hexyl] | 1.2 |
| A278 | [n-heptyl] | 1.5 |
| A279 | [cyclopentyl] | 4.5 |
| A280 | [cyclobutyl-CH2-] | 3.4 |
| A281 | [cyclopentyl-CH2-] | 1.8 |
| A282 | [4-pyridyl-CH2-] | N.A. |
| A283 | [3-pyridyl-CH2-] | N.A. |
| A284 | [2-pyridyl-CH2-] | N.A. |
| A285 | [6-(HOCH2)-2-pyridyl-CH2-] | N.A. |
| A286 | [5-CF3-2-furyl-CH2-] | 0.3 |

TABLE 3-continued

Inhibition activities of representative Class A compounds.

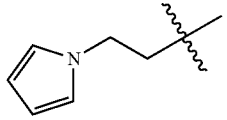 [SMILES: *CCn1cccc1]

| Compound | R | IC$_{50}$ (μM) |
|---|---|---|
| A287 | 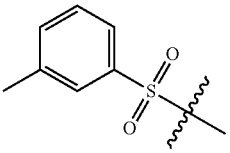 [SMILES: *S(=O)(=O)c1cccc(C)c1] | N.A. |
| A288 | 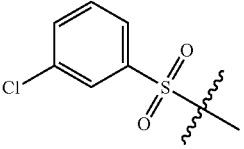 [SMILES: *S(=O)(=O)c1cccc(Cl)c1] | N.A. |
| A289 | | N.A |

Figure 9:
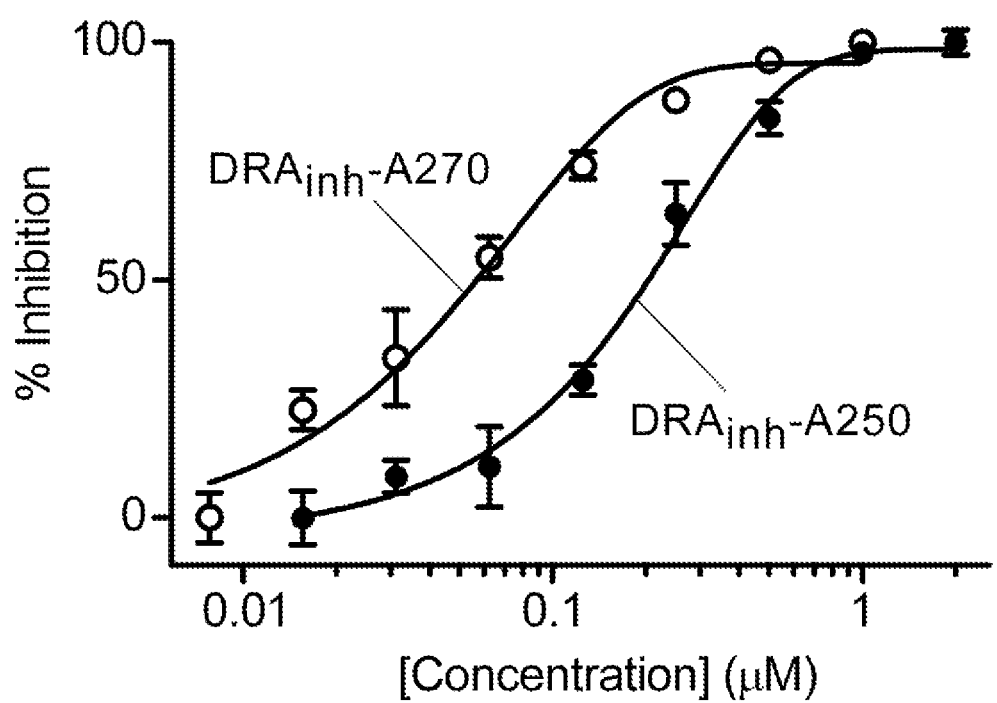
FIG. 9. The concentration-inhibition curves for Compound A1 ($DRA_{inh}$-A250) and $DRA_{inh}$-A270 for slc26a3-mediated $Cl^-/I^-$-exchange. $DRA_{inh}$-A270 had four-fold improved potency (~50 nM $IC_{50}$) compared to Compound A1.

FIG. 9 shows the concentration-inhibition curves of two representative compounds, namely, DRAinh-A250 and DRAinh-A270. DRAinh-A270 had four-fold improved potency (~50 nM IC50) compared to DRAinh-A250. Table 3 below shows additional compounds of Formula (I) and their IC$_{50}$.

Example 14

Pharmacokinetic Studies

Figure 10:
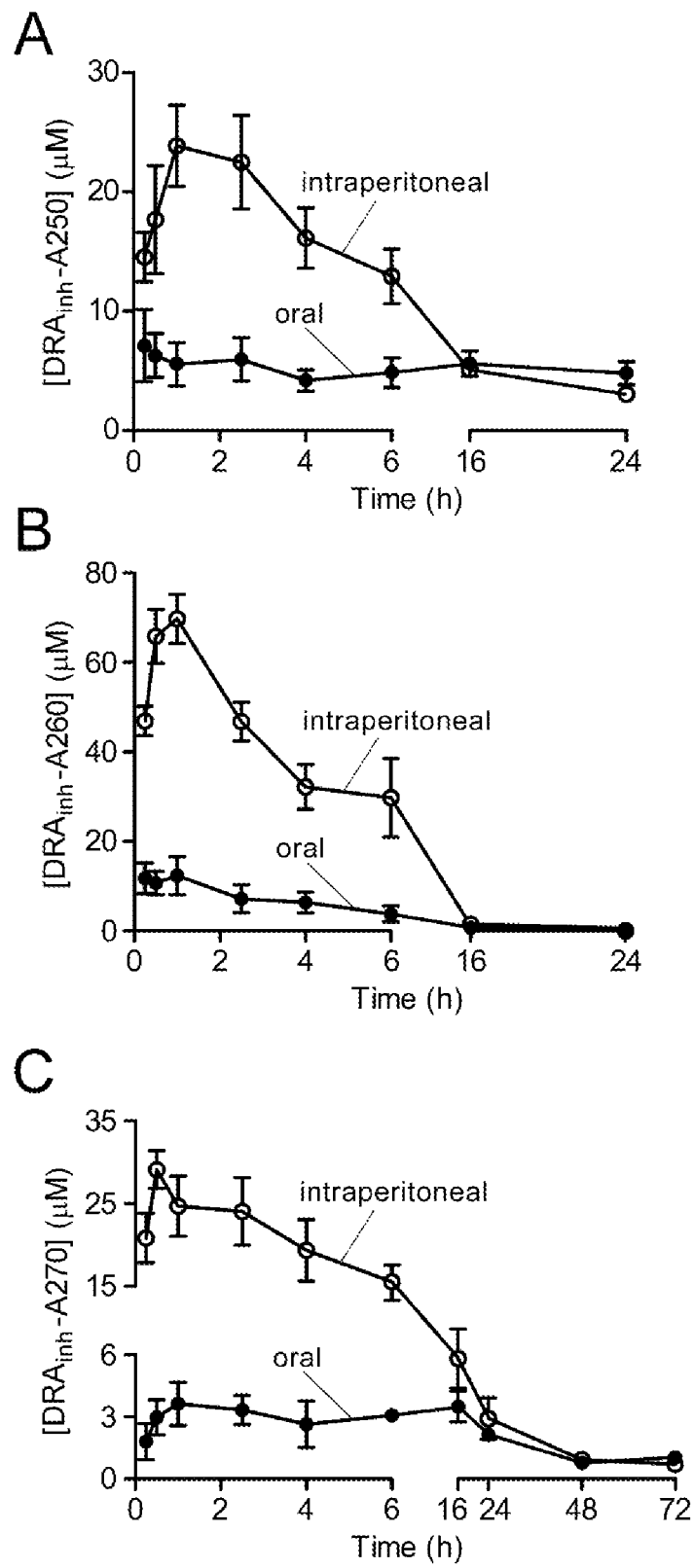
FIG. 10. Pharmacokinetics of DRA inhibitors after single dose intraperitoneal or oral administration. A. Serum concentrations of Compound A1 ($DRA_{inh}$-A250) after 5 mg/kg administration. B. Serum concentrations of $DRA_{inh}$-A260 after 5 mg/kg administration. C. Serum concentrations of $DRA_{inh}$-A270 after 10 mg/kg administration.

Pharmacokinetics of the Compound A1 (DRAinh-A250) and analogs (DRA$_{inh}$-A260 and DRA$_{inh}$-A270) was determined in mice. After single dose intraperitoneal or oral administration (5 mg/kg for Compound A1 and DRA$_{inh}$-A260, 10 mg/kg for DRA$_{inh}$-A270), blood samples were collected via retro-orbital puncture at different time points and serum was separated by centrifugation. Compound concentrations were measured in serum using LC/MS. FIGS. 10A, 10B, 10C show the respective serum concentration of Compound A1 (FIG. 10A), DRA$_{inh}$-A260 (FIG. 10B) and DRA$_{inh}$-A270 (FIG. 10C) after single oral or intraperitoneal administration at zero time (n=3 mice per compound per administration route). Compound A1 had predicted therapeutic levels for at least 24 hours after single dose oral or intraperitoneal administration. DRA$_{inh}$-A260 had high serum levels initially after single dose oral or intraperitoneal administration. However, the concentrations were not sustained with almost complete disappearance of compound from serum at 16 hours. DRA$_{inh}$-A270 had predicted therapeutic concentrations for several days after single dose oral or intraperitoneal administration and serum concentrations of DRA$_{inh}$-A270 were approximately 1 μM even 72 hours after single dose oral or intraperitoneal dosing. Under these conditions oral bioavailability was 54% for Compound A1, 16% for DRA$_{inh}$-A260, and 39% for DRA$_{inh}$-A270. (mean±SEM): 53.9±6.5% for Compound A1, 16.4±6.6% for DRA$_{inh}$-A260, and 39.3±3.5% for DRA$_{inh}$-A270.

Example 15

Efficacy Study in Mouse Constipation Model

Figure 11:
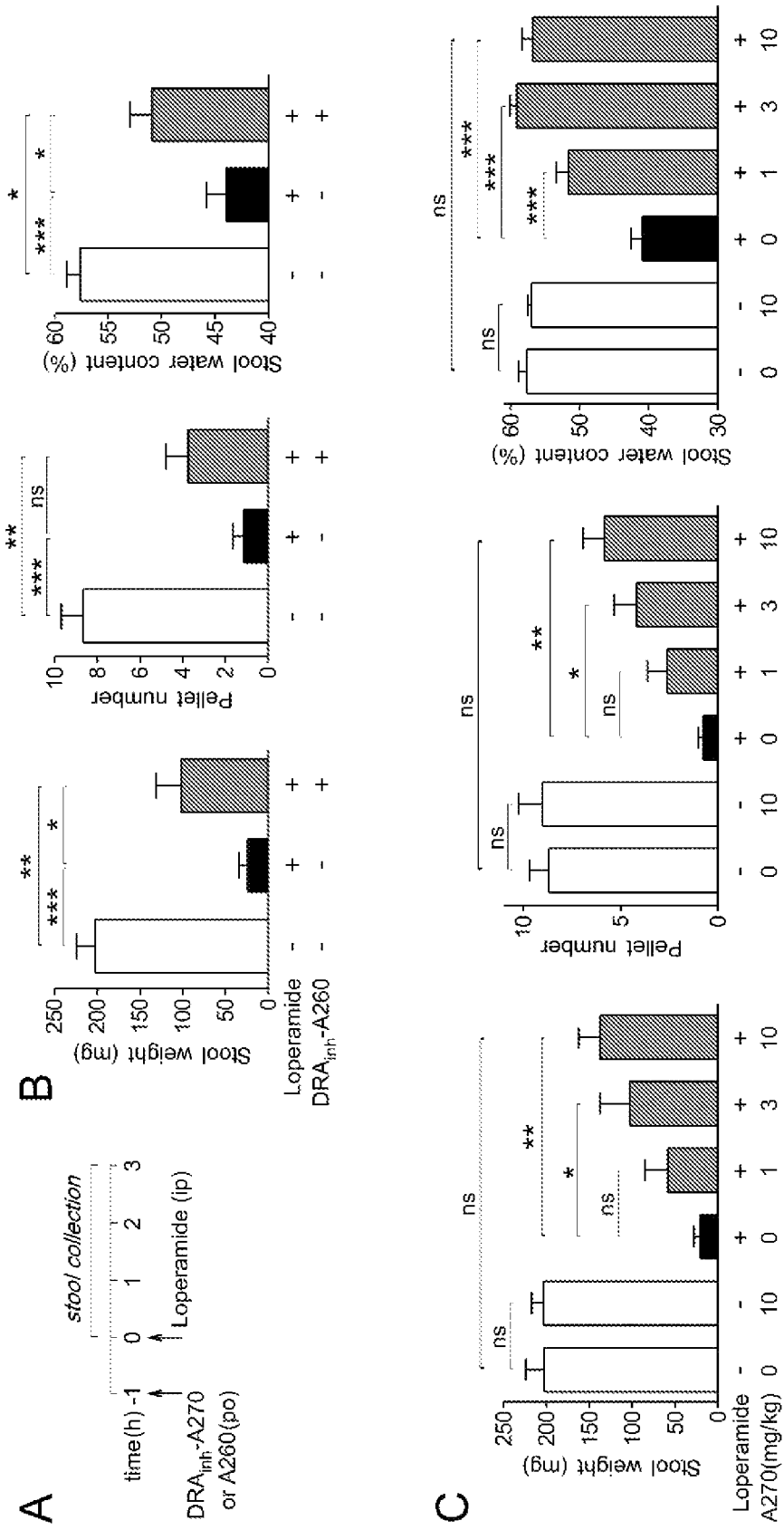
FIG. 11. Efficacy of DRA inhibitors in loperamide-induced constipation model in mice. A. Experimental protocol. B. $DRA_{inh}$-A260 improves 3-hour stool weight, pellet number and water content in loperamide-treated mice (n=4-6 mice per group). C. Dose-dependence of $DRA_{inh}$-A270 effect (n=5-8 mice per group). Comparisons made with one-way analysis of variance with post-hoc Newman Keuls multiple comparisons test, *p<0.05, p<0.01, *p<0.001, ns: not significant. ip: intraperitoneal, po: oral, A270: $DRA_{inh}$-A270.

Constipation Model in MiceDRA$_{inh}$-A260 and DRA$_{inh}$-A270 were tested in a loperamide-induced constipation model in mice. Female CD1 mice (age 8-10 weeks) were administered loperamide (0.3 mg/kg, intraperitoneally, in 5% ethanol in PBS, 0.1 mg/mL final concentration) to produce constipation and vehicle in control mice. DRA$_{inh}$-A260 (5 mg/kg, in saline with 5% DMSO and 10% Kolliphor HS 15) or DRA$_{inh}$-A270 (1, 3 or 10 mg/kg, in PBS with 5% DMSO and 20% (2-hydroxypropyl)-β-cyclodextrin) or vehicle alone were administered by oral gavage 1 hour before loperamide (FIG. 11A). After loperamide injection, mice were placed individually in metabolic cages with free access to food and water. Stool samples were collected for 3 hours, and total stool weight and number of fecal pellets were quantified. To measure stool water content, stool samples were dried at 80° C. for 24 hours and water content was calculated as [wet weight-dry weight]/wet weight.

FIG. 11B shows the efficacy of DRA$_{inh}$-A260 in improving stool weight, pellet number and water content in loperamide-treated mice (n=4-6 mice per group, comparisons made with one-way analysis of variance with post-hoc Newman Keuls multiple comparisons test, *$p<0.05$, $p<0.01$, *$p<0.001$, ns: not significant).

FIG. 11C shows DRA$_{inh}$-A270 dose-dependence in normalizing stool weight and pellet number, and water content in loperamide-treated mice. (n=5-8 mice per group, comparisons made with one-way analysis of variance with post-hoc Newman Keuls multiple comparisons test, *$p<0.05$, $p<0.01$, *$p<0.001$, ns: not significant).

FIG. 11C also shows that DRA$_{inh}$-A270 did not affect stool parameters or cause diarrhea in control mice (not treated with loperamide) at high dose (10 mg/kg). These results demonstrate efficacy of DRA$_{inh}$-A260 and DRA$_{inh}$-A270 in a mouse model of constipation induced by loperamide, and show that DRA$_{inh}$-A270 normalizes stool water content even at low doses.

Example 16

Efficacy Study in Acute Hyperoxaluria Model

Figure 12:
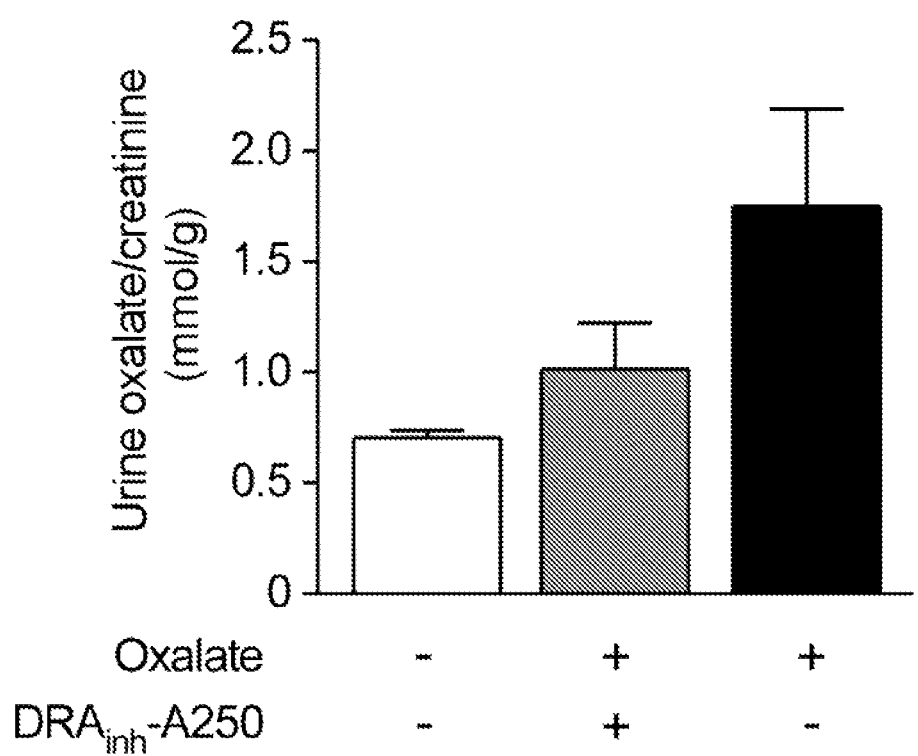
FIG. 12. Efficacy of Compound A1($DRA_{inh}$-A250) in acute hyperoxaluria induced by oral sodium oxalate administration (n=3-4 mice per group).

The efficacy of Compound A1 (DRA$_{inh}$-A250) and DRA$_{inh}$-A270 were tested in models of acute hyperoxaluria and oxalate nephropathy in mice. To induce acute hyperoxaluria, mice were given sodium oxalate (1 μmol/kg) with or without 5 mg/kg Compound A1 by oral gavage at zero time and urine was collected for the next 4 hours in metabolic cages. A group of mice were used as controls and treated with vehicle only (no sodium oxalate or DRA inhibitor) and their urine was collected for 4 hours in metabolic cages as well. Using the 4 hour urine samples, urine oxalate/creatinine ratio was determined to quantify urinary oxalate excretion. FIG. 12 shows that oral sodium oxalate treatment increased urine oxalate/creatinine ratio by more than 2-fold, thus causing hyperoxaluria; treatment with Compound A1 largely prevented hyperoxaluria in this model.

Figure 13:
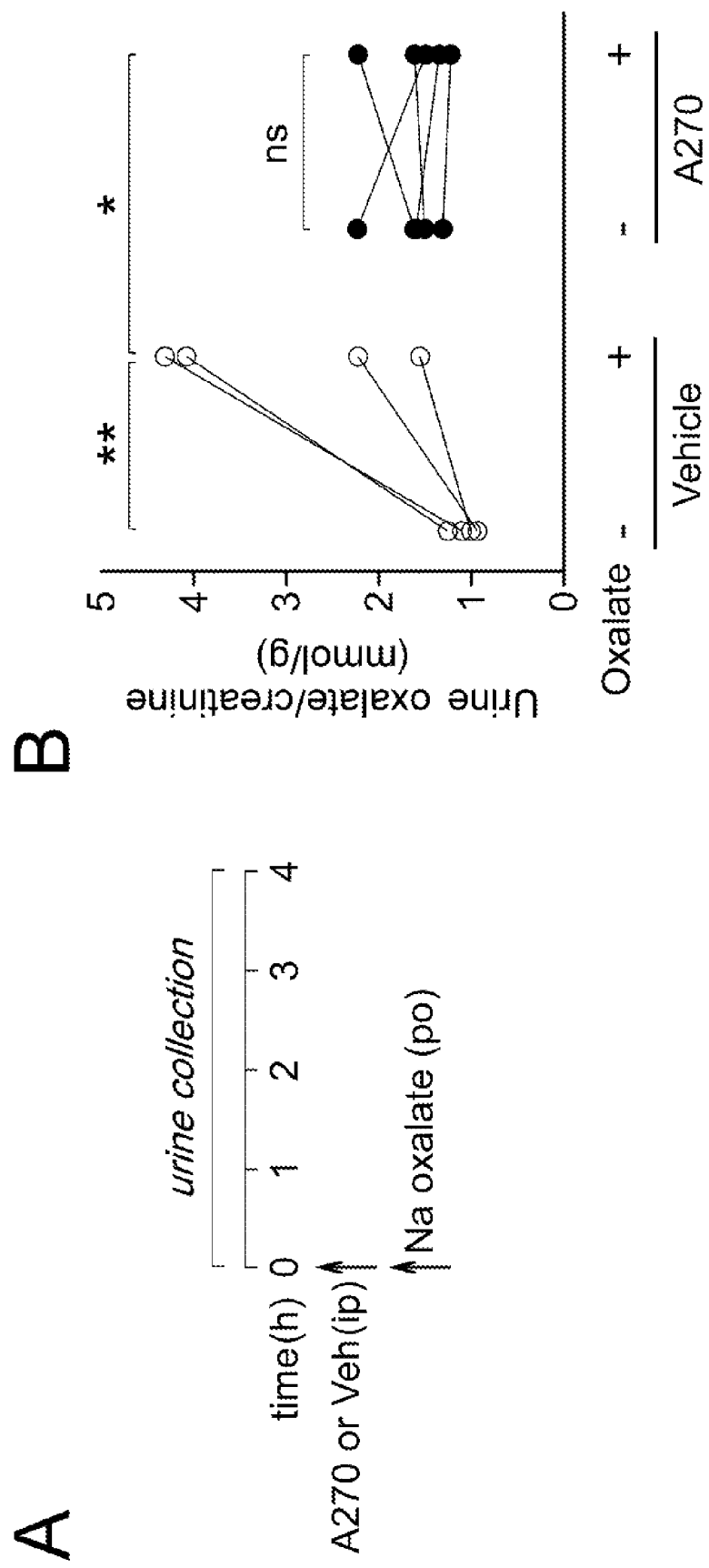
FIG. 13. Efficacy of $DRA_{inh}$-A270 in acute hyperoxaluria induced by oral sodium oxalate administration. A. Experimental protocol. B. Urine oxalate/creatinine ratios in mice (before and after oral sodium oxalate treatment) treated with $DRA_{inh}$-A270 or vehicle (n=4-5 mice per group). Comparisons made with one-way analysis of variance with post-hoc Newman Keuls multiple comparisons test, *p<0.05, **p<0.01, ns: not significant. ip: intraperitoneal, po: oral, A270: $DRA_{inh}$-A270, Veh: vehicle.

Similar experiments were performed for DRA$_{inh}$-A270 in the acute hyperoxaluria model. For these experiments mice were first placed in metabolic cages to collect urine for 4 hours without any treatment. After this initial collection, the mice were treated with DRA$_{inh}$-A270 (10 mg/kg) or vehicle intraperitoneally, and given sodium oxalate (2.5 μmol/kg, in water) by oral gavage at zero time. Urine was collected for the next 4 hours in metabolic cages. FIG. 13A shows the experimental protocol and FIG. 13B shows 4-hour urine oxalate/creatinine ratios in mice under these experimental conditions. Oral sodium oxalate increased urine oxalate/creatinine ratio more than 2-fold on average and treatment with DRA$_{inh}$-A270 largely prevented hyperoxaluria in this model.

Example 17

Efficacy Study in Oxalate Nephropathy Model

Figure 14:
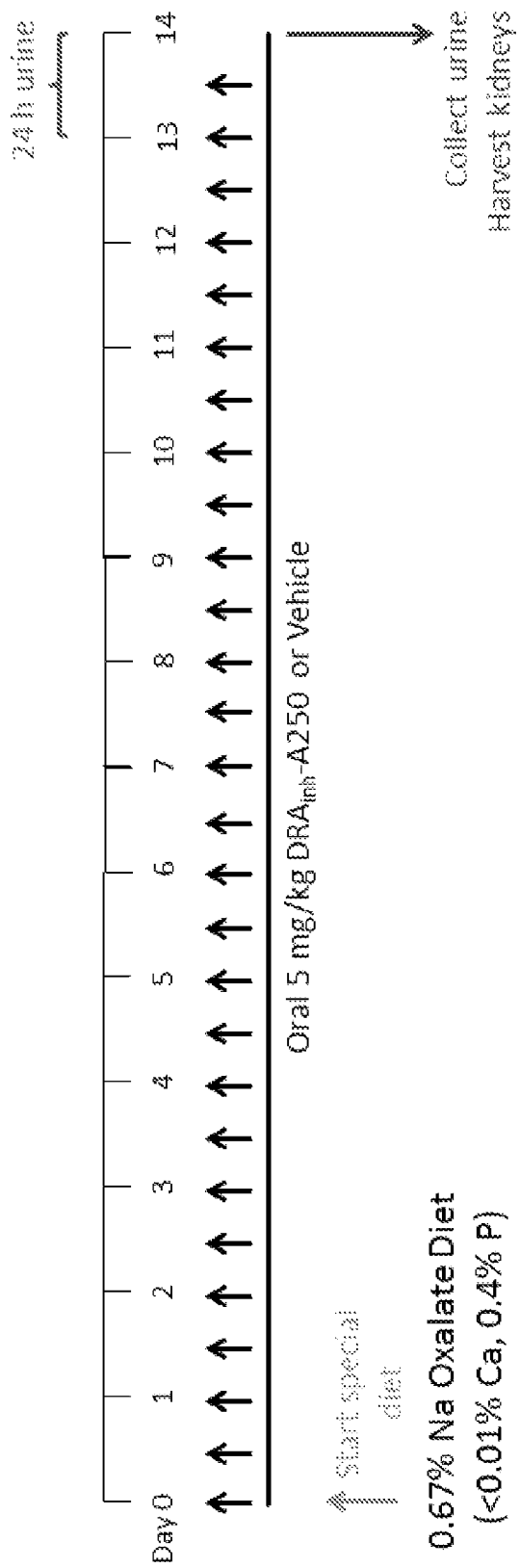
FIG. 14. Experimental protocol for inducing oxalate nephropathy model in mice.
Figure 15:
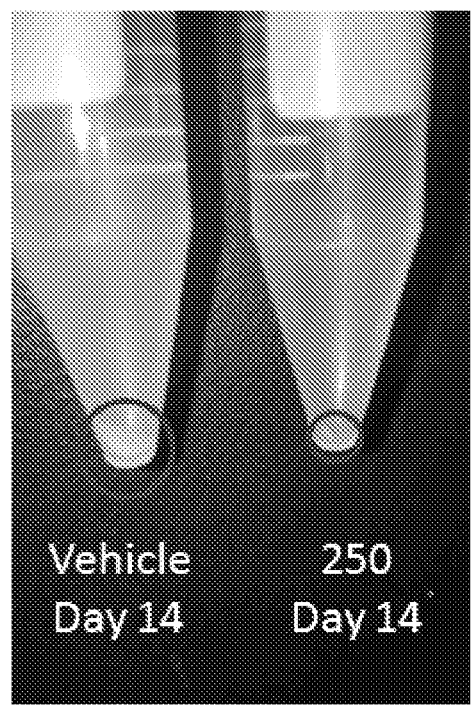
FIG. 15. Compound A1($DRA_{inh}$-A250) treatment greatly reduces urine sediment in oxalate nephropathy model. A representative photo showing insoluble urine sediment (circled) in vehicle and Compound A1-treated mice at Day 14 of the oxalate nephropathy model (representative of 4-5 mice per group).

To induce oxalate nephropathy, mice were fed with high oxalate (0.67%) and low calcium (<0.01%) diet as described (*Am J Physiol Renal Physiol* 310: F785-F795, 2016). FIG. 14 shows the experimental protocol. Mice were started high oxalate diet at Day 0 and treated with Compound A1 (5 mg/kg) or vehicle by oral gavage twice daily starting at Day 0. At Day 14, urine was collected for 24 hours in metabolic cages and centrifuged to examine urine sediment, then mice were euthanized and kidneys were used for histological analysis. FIG. 15 shows that vehicle-treated mice had large amount of insoluble sediment, which was greatly reduced in mice treated with Compound A1.

Figure 16:
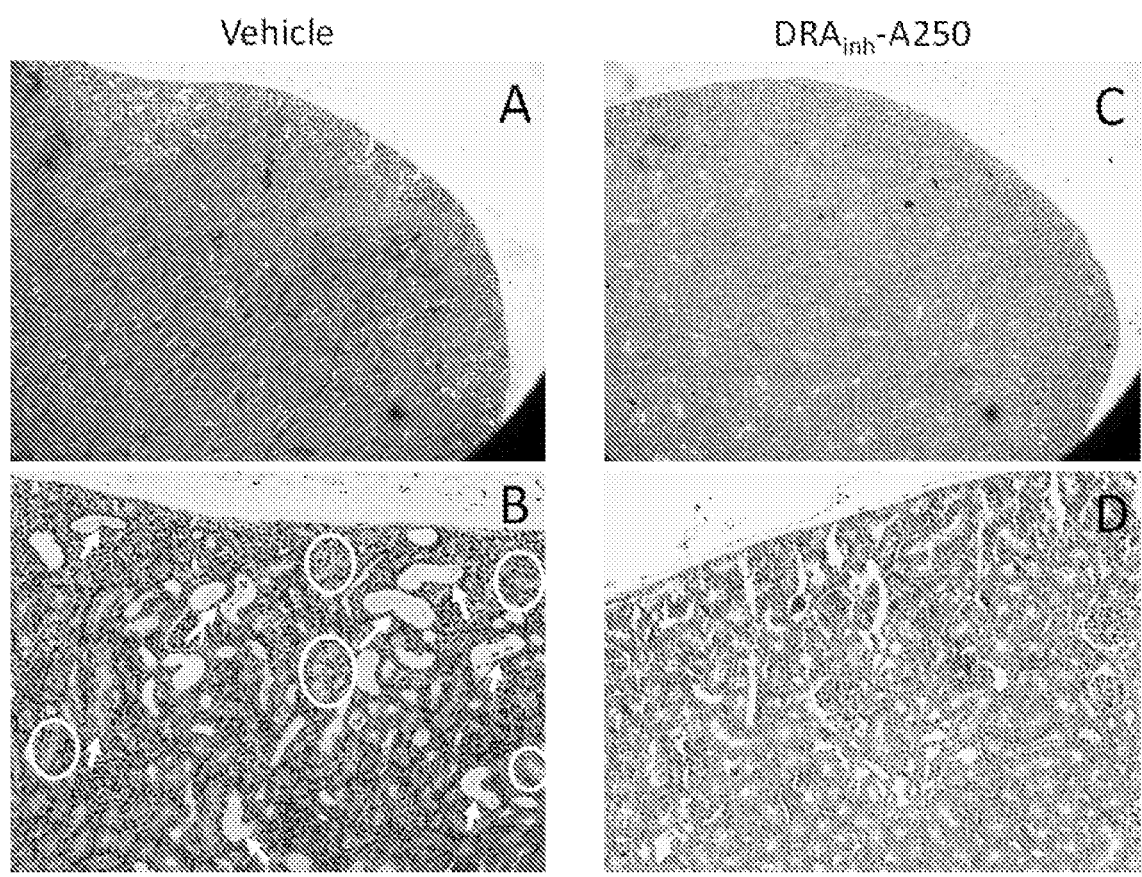
FIG. 16. Compound A1($DRA_{inh}$-A250) treatment prevents renal damage in the oxalate nephropathy model. A. and B. Vehicle-treated mice at Day 14 of the oxalate nephropathy model had marked renal damage (inflammation-darkened areas, necrosis-circled areas, tubular casts-arrows pointed areas) (representative of 5 mice), 4× and 10× magnification in A and B, respectively. C and D. Compound A1-treated mice had normal appearing kidneys with no significant damage (representative of n=4 mice), 4× and 10× magnification in C and D, respectively.
Figure 17:
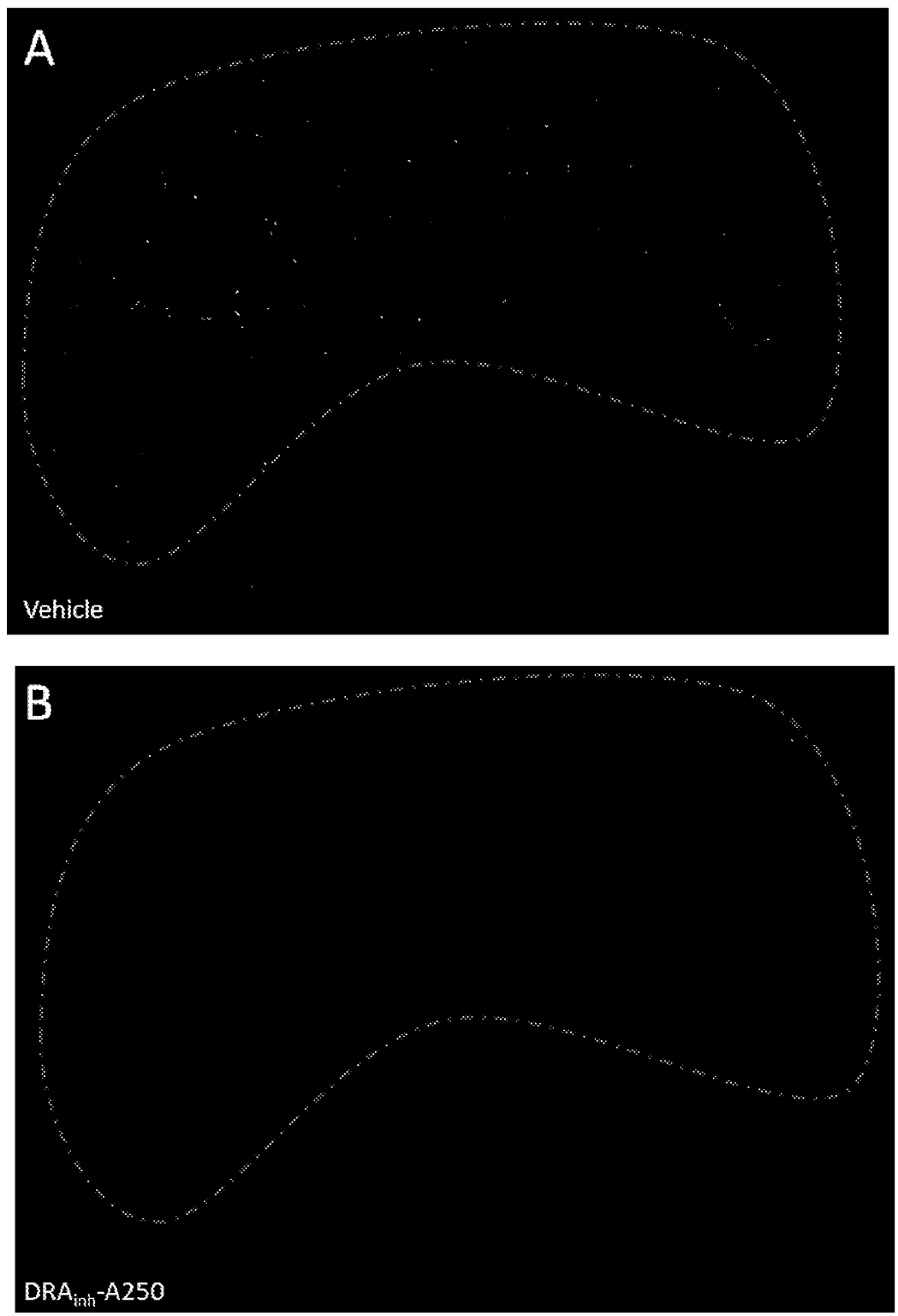
FIG. 17. Compound A1 treatment prevents renal crystal deposition in the oxalate nephropathy model. A. Whole kidney (inside dashed line) in vehicle-treated mouse at Day 14 examined under polarized light (4× magnification), white dots represent renal crystal deposition (representative of n=5 mice). B. Whole kidney (inside dashed line) in Compound A1-treated mouse at Day 14 examined under polarized light (4× magnification), white dots represent renal crystal deposition (representative of n=4 mice).

The kidneys harvested at Day 14 were examined for kidney damage using H & E staining, and for crystal deposition using polarized light microscopy. FIGS. 16A and 16B shows significant kidney damage in vehicle-treated mice and FIGS. 16C and 16D shows prevention of kidney damage by Compound A1 treatment. FIG. 17A shows widespread crystal deposition in kidneys of vehicle-treated mice and FIG. 17B shows prevention of crystal deposition by Compound A1 treatment.

Figure 18:
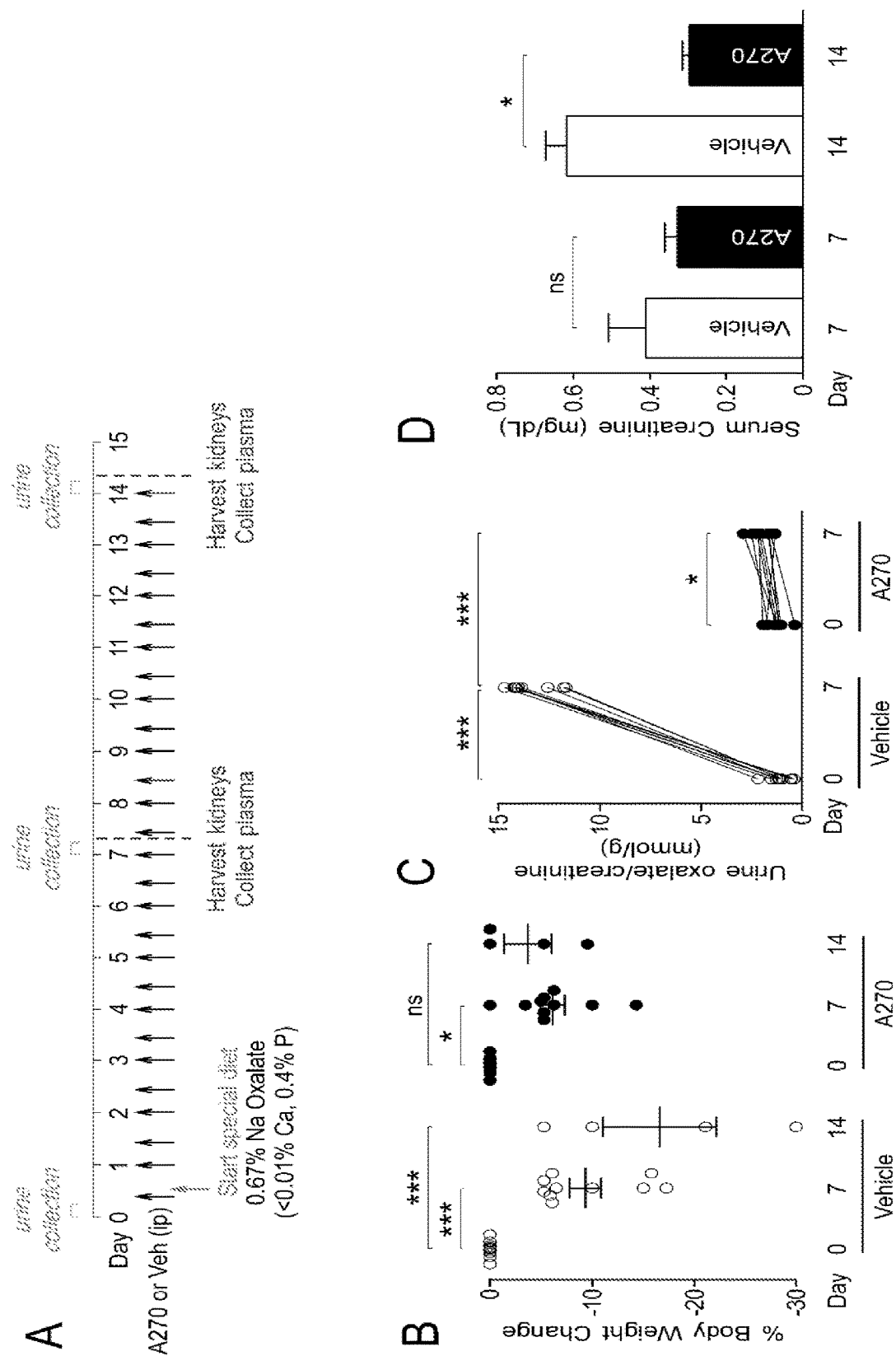
FIG. 18. $DRA_{inh}$-A270 prevents weight loss, hyperoxaluria and renal failure in the oxalate nephropathy model. A. Experimental protocol. B. Percent change in body weight compared to Day 0 in mice treated with vehicle or $DRA_{inh}$-A270 (n=4-10 mice per group per time point). C. 3-hour urine oxalate/creatinine ratio on Day 0 and Day 7 in mice treated with vehicle or $DRA_{inh}$-A270 (10 mice per group per time point). D. Serum creatinine at Day 7 and 14 in mice treated with vehicle or $DRA_{inh}$-A270 (n=4-6 mice per group per time point). Comparisons made with one-way analysis of variance with post-hoc Newman Keuls multiple comparisons test, *$p<0.05$, ***$p<0.001$, ns: not significant. ip: intraperitoneal, A270: $DRA_{inh}$-A270, Veh: vehicle.

Similar experiments in oxalate nephropathy model were performed using DRA$_{inh}$-A270. For these experiments mice had 3-hour urine collections at Day 0, 7 and 14. High oxalate diet was started on Day 0 after initial urine collection and mice were given DRA$_{inh}$-A270 or vehicle intraperitoneally twice daily for 14 days. FIG. 18A shows the experimental protocol. FIG. 18B shows that vehicle-treated mice had significant weight loss (sign of disease severity) at Day 7 and Day 14 compared to Day 0; DRA$_{inh}$-A270-treated mice maintained their weight better during the experiments. FIG. 18C shows that vehicle-treated mice had approximately 7-fold increased urine oxalate/creatinine ratio at Day 7 compared to Day 0; DRA$_{inh}$-A270 treatment largely prevented development of hyperoxaluria. FIG. 18D shows at Day 14, vehicle-treated mice had significantly higher serum creatinine levels (suggesting impaired kidney function); DRA$_{inh}$-A270-treated mice had normal serum creatinine and thus normal renal function. These results overall suggest that DRA$_{inh}$-A270 treatment prevents development of renal failure in high oxalate diet-induced oxalate nephropathy model in mice.

In summary, these results suggest that DRA inhibitors prevent hyperoxaluria in various mouse models, supporting the efficacy of the DRA inhibitors in prevention of calcium oxalate kidney stones and treatment of hyperoxaluria related to various conditions including enteric hyperoxaluria (due to gastric bypass surgery, intestinal resection, inflammatory bowel disease, pancreatic insufficiency or other malabsorption syndromes) and primary hyperoxalurias.

The various embodiments described above can be combined to provide further embodiments. All U.S. patents, U.S. patent application publications, U.S. patent applications, foreign patents, foreign patent applications, and non-patent publications referred to in this specification are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A pharmaceutical composition comprising a physiologically acceptable excipient and a compound of Formula (I):

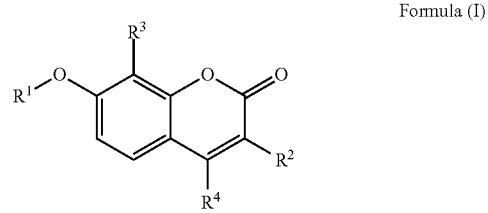

Formula (I)

or a pharmaceutically acceptable salt, isotopic form, stereoisomer or prodrug thereof, wherein:
$R^1$ is wherein:
X is $C_3$-$C_5$ cycloalklyl, bromo, chloro, iodo, haloalklyl, $NO_2$, or haloalkoxy; and
n is 1, 2, 3, 4 or 5;
$R^2$ is carboxy$C_1$-$C_3$alkyl;
$R^3$ is $C_1$-$C_4$ alkyl; and
$R^4$ is $C_1$-$C_4$ alkyl.

2. The pharmaceutical composition of claim 1, wherein X is bromo, chloro, iodo, cyclopropyl, $CF_3$, or $NO_2$ and n is 1 or 2.

3. The pharmaceutical composition of claim 1, wherein $R^1$ has one of the following structures:

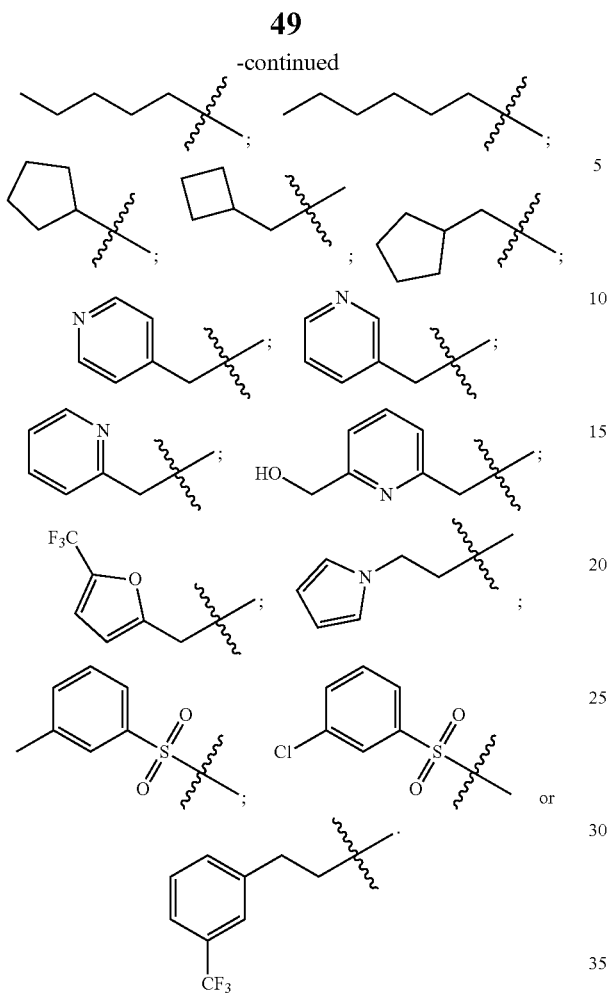

4. The pharmaceutical composition of claim 1, wherein $R^2$ has one of the following structures:

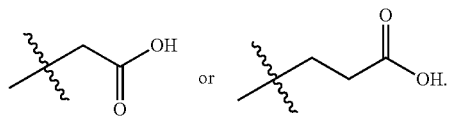

5. The pharmaceutical composition of claim 1 wherein the compound is represented by Formula (Ia):

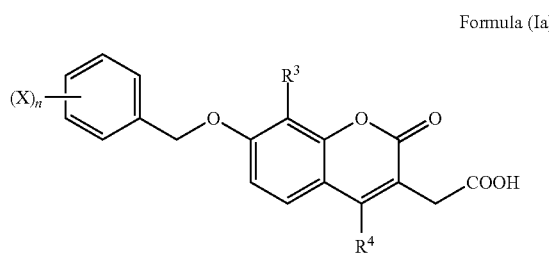

Formula (Ia)

wherein, X is $C_3$-$C_5$ cycloalkyl, bromo, chloro, iodo, haloalkyl, $NO_2$, or haloalkoxy; and n is 1, 2, or 3.

6. A pharmaceutical composition comprising a physiologically acceptable excipient and a compound having one of the following structures:

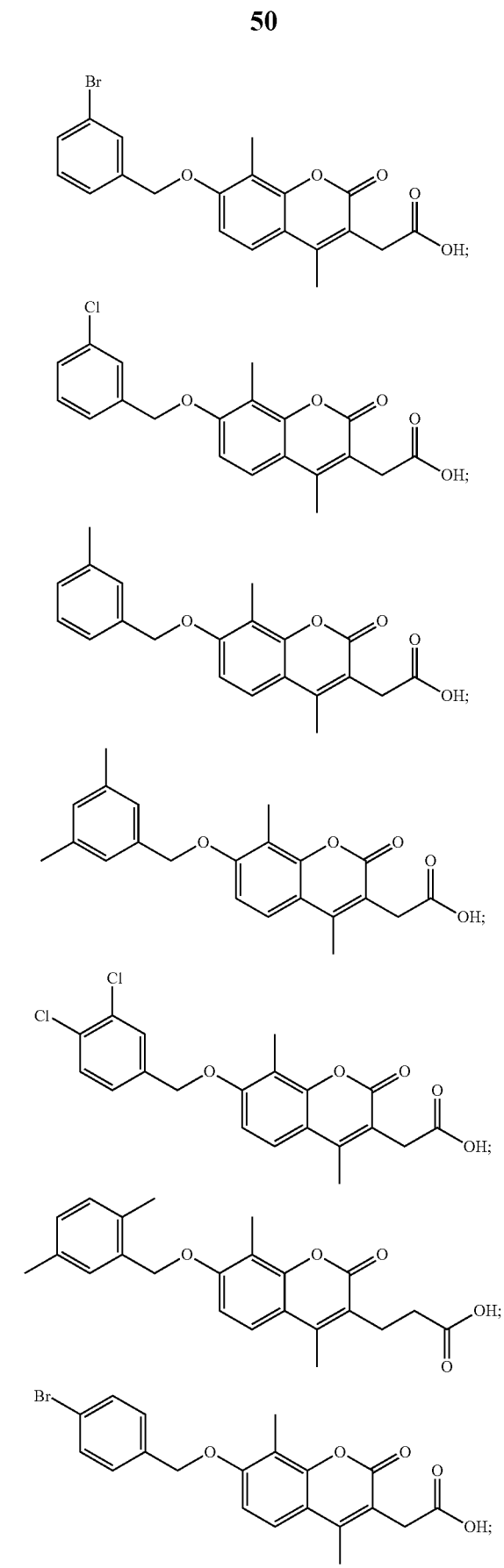

51
-continued
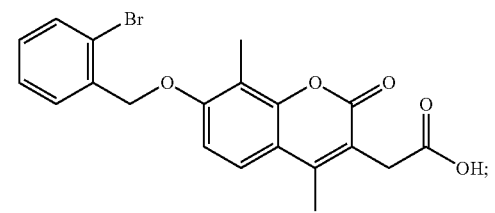
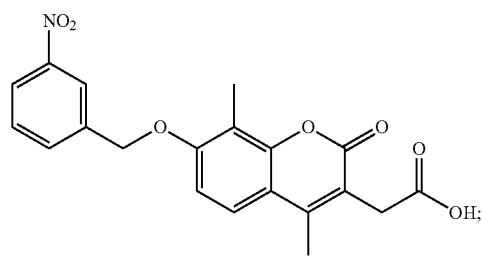
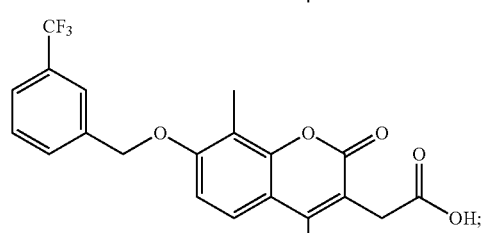
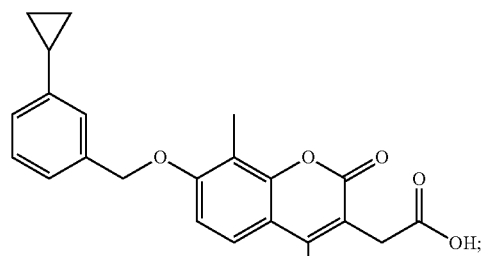
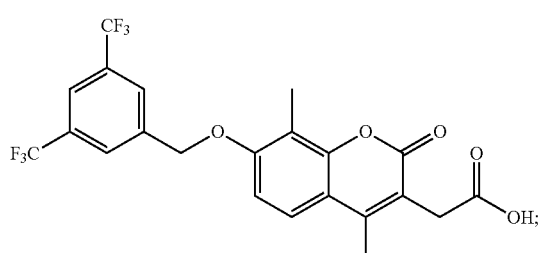
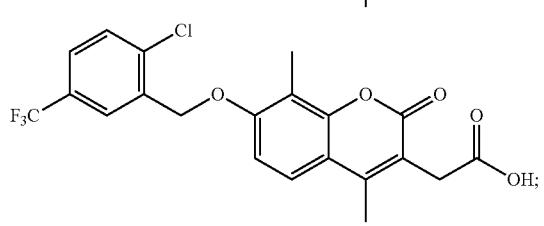
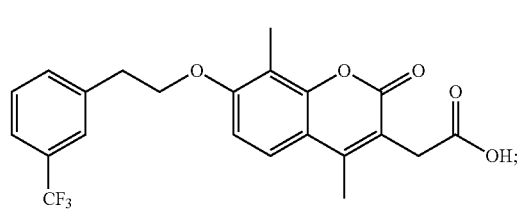
52
-continued
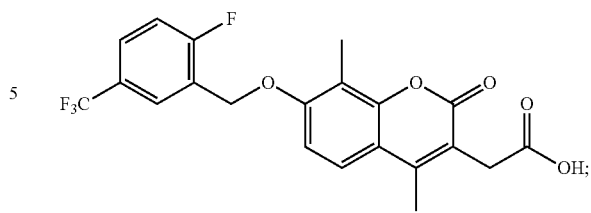
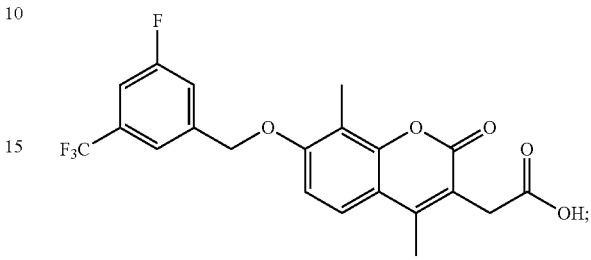
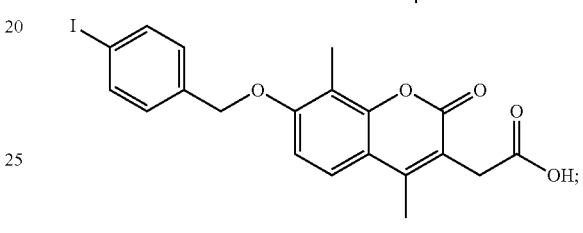
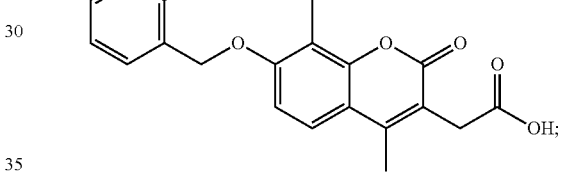
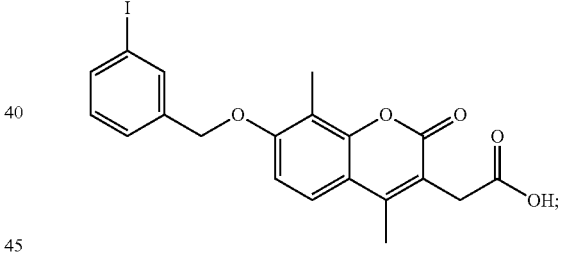
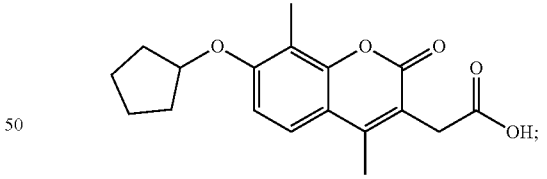
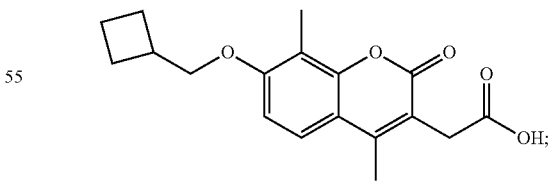
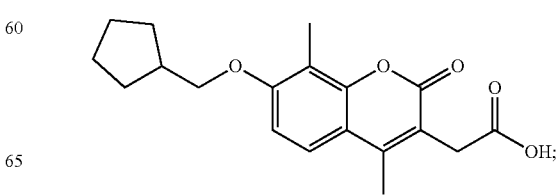

-continued

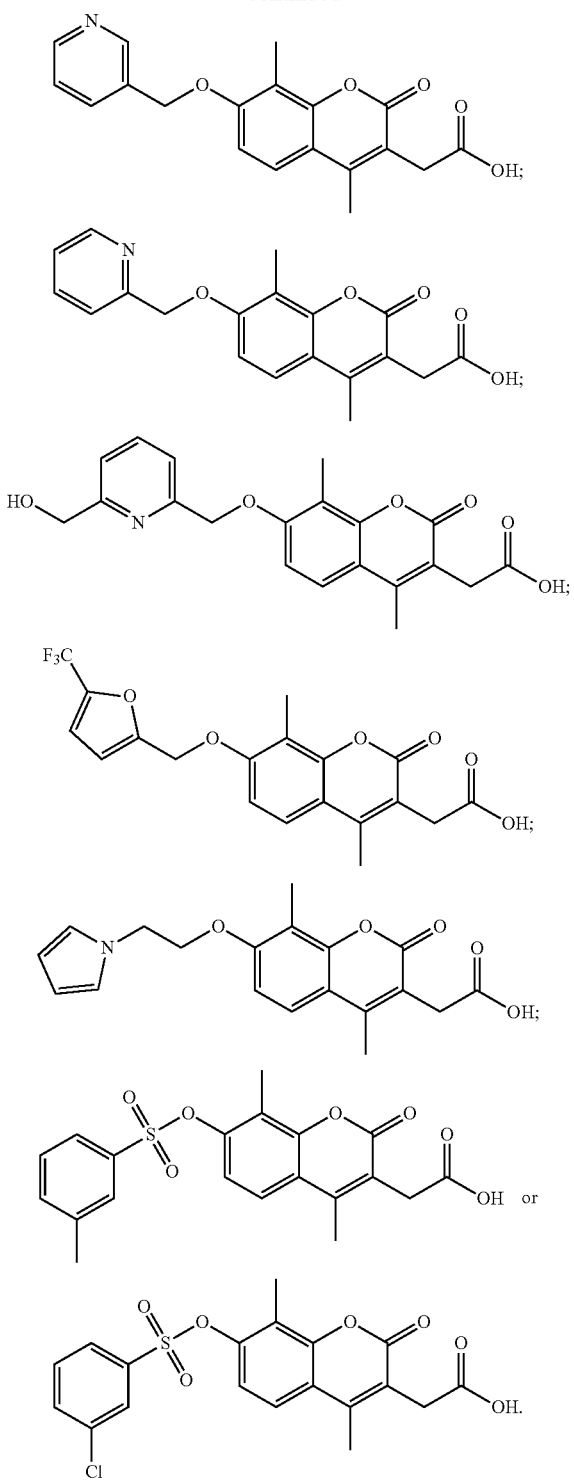

7. A method for treating a condition, disease, or disorder associated with SLC26A3-mediated Cl⁻, HCO₃⁻, or oxalate exchange in a subject, wherein the condition, disease, or disorder is constipation or hyperoxaluria, the method comprising administering to the subject a pharmaceutical composition comprising a physiologically acceptable excipient and a compound of Formula (I):

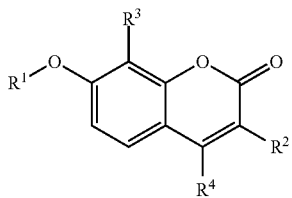

Formula (I)

or a pharmaceutically acceptable salt, isotopic form, stereoisomer or prodrug thereof, wherein:

$R^1$ is

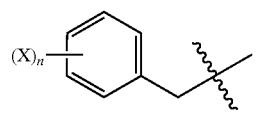

wherein:
  X is $C_3$-$C_5$ cycloalkyl, bromo, chloro, iodo, haloalkyl, $NO_2$, or haloalkoxy; and
  n is 1, 2, 3, 4 or 5;
$R^2$ is carboxy$C_1$-$C_3$alkyl;
$R^3$ is $C_1$-$C_4$ alkyl; and
$R^4$ is $C_1$-$C_4$ alkyl.

8. The method of claim 7 wherein the condition, disease, or disorder is chronic idiopathic constipation (CIC), opioid-induced constipation (OIC), constipation-predominant irritable bowel syndrome (IBS-C), kidney stone disease, CF-associated constipation, meconium ileus, distal intestinal obstruction syndrome, calcium oxalate kidney stone disease, enteric hyperoxaluria, or primary hyperoxaluria.

9. The method of claim 7, wherein the compound is represented by Formula (Ia):

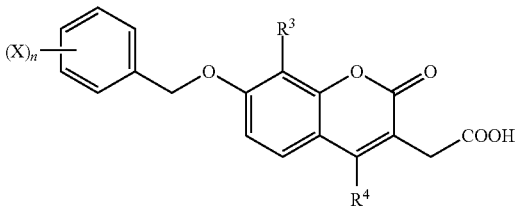

Formula (Ia)

wherein, X is $C_3$-$C_5$ cycloalkyl, bromo, chloro, iodo, haloalkyl, $NO_2$, or haloalkoxy; and n is 1, 2, or 3.

10. The method of claim 9, wherein the compound is:

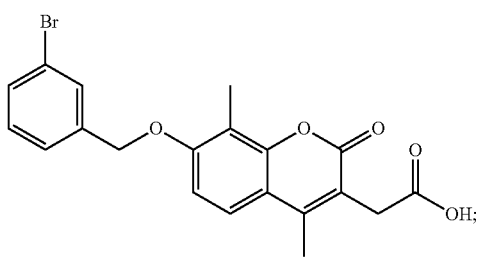

-continued
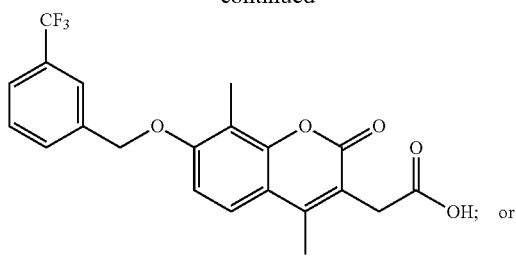
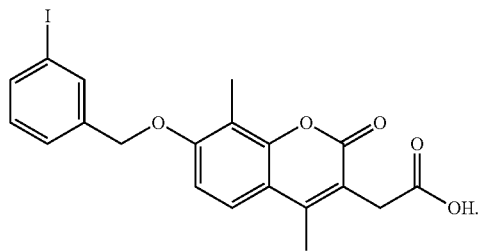
11. The method of claim 7, wherein the compound of Formula (I) is combined with an NHE3 inhibitor.
12. The method of claim 11 wherein the NHE3 inhibitor is tenapanor.
13. A compound having one of the following structures:
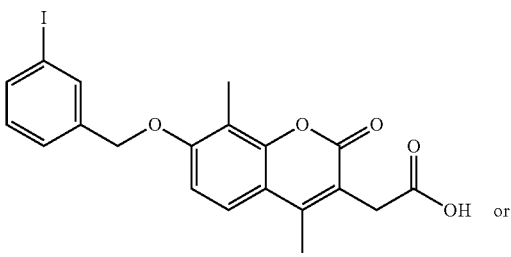
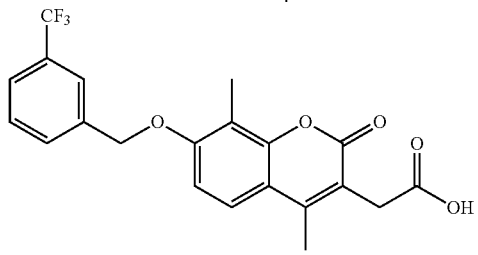
or a pharmaceutically acceptable salt, isotopic form, stereoisomer or prodrug thereof.
* * * * *